(12) United States Patent
Marchini et al.

(10) Patent No.: US 10,406,185 B2
(45) Date of Patent: *Sep. 10, 2019

(54) CANCER THERAPY WITH A PARVOVIRUS COMBINED WITH A BCL-2 INHIBITOR

(71) Applicants: DEUTSCHES KREBSFORSCHUNGSZENTRUM, Heidelberg (DE); RUPRECHT-KARLS-UNIVERSITÄT HEIDELBERG, Heidelberg (DE)

(72) Inventors: Antonio Marchini, Heidelberg (DE); Junwei Li, Eppelheim (DE); Lea Schroeder, Heidelberg (DE); Jean Rommelaere, Heidelberg (DE); Karsten Geletneky, Heidelberg (DE)

(73) Assignees: DEUTSCHES KREBSFORSCHUNGSZENTRUM, Heidelberg (DE); RUPRECHT-KARLS-UNIVERSITAT HEIDELBERG, Heidelberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/856,241

(22) Filed: Dec. 28, 2017

(65) Prior Publication Data

US 2018/0117104 A1 May 3, 2018

Related U.S. Application Data

(63) Continuation of application No. 14/960,608, filed on Dec. 7, 2015, now Pat. No. 9,889,169, which is a continuation-in-part of application No. PCT/EP2014/002001, filed on Jul. 22, 2014.

(30) Foreign Application Priority Data

Jul. 22, 2013 (EP) .................................. 13003664

(51) Int. Cl.
| | | |
|---|---|---|
| *A61K 35/768* | (2015.01) | |
| *A61K 45/06* | (2006.01) | |
| *A61K 31/495* | (2006.01) | |
| *A61K 31/5377* | (2006.01) | |
| *A61K 31/63* | (2006.01) | |
| *A61K 31/635* | (2006.01) | |

(52) U.S. Cl.
CPC ......... *A61K 35/768* (2013.01); *A61K 31/495* (2013.01); *A61K 31/5377* (2013.01); *A61K 31/63* (2013.01); *A61K 31/635* (2013.01); *A61K 45/06* (2013.01); *C12N 2750/14332* (2013.01)

(58) Field of Classification Search
CPC .. A61K 2039/5254; C12N 2760/12234; C12N 2760/18722; C12N 2770/24143; C12N 2800/22; C12N 2830/00; C07K 14/005; C07K 14/175; G01N 2333/175
See application file for complete search history.

(56) References Cited

U.S. PATENT DOCUMENTS

| | | |
|---|---|---|
| 8,414,883 B2 | 4/2013 | Rommelaere et al. |
| 2011/0020287 A1 | 1/2011 | Rommelaere et al. |
| 2013/0058899 A1 | 3/2013 | Marchini et al. |
| 2014/0234261 A1 | 8/2014 | Rommelaere et al. |
| 2015/0030567 A1 | 1/2015 | Marchini et al. |

FOREIGN PATENT DOCUMENTS

| | | |
|---|---|---|
| WO | 2009/083232 | 7/2009 |
| WO | 2011/113600 | 9/2011 |

OTHER PUBLICATIONS

International Search Report dated Dec. 23, 2014, which issued during prosecution of International Application No. PCT/EP2014/002001.
Written Opinion of the International Searching Authority dated Dec. 23, 2014, which issued during prosecution of International Application No. PCT/EP2014/002001.
International Preliminary Report on Patentability and Written Opinion of the International Searching Authority dated Jan. 26, 2016, which issued during prosecution of International Application No. PCT/EP2014/002001.
Bajwa, et al. "Inhibitors of the anti-apoptotic Bcl-2 proteins: a patent review" Expert Opinion on Therapeutic Patents 22(1):37-55, Jan. 2012.
Del Gaizo Moore, et al. "Chronic lymphocytic leukemia requires BCL2 to sequester prodeath BIM, explaining sensitivity to BCL2 antagonist ABT-737" Journal of Clinical Investigation 117(1):112-121, Jan. 2007.
Di Piazza, et al. "Cytosolic activation of cathepsins mediates parvovirus H-1-induced killing of cisplatin and TRAIL-resistant glioma cells" Journal of Virology 81(8):4186-4198, Apr. 2007.
Moehler, et al. "Activation of the human immune system by chemotherapeutic or targeted agents combined with the oncolytic parvovirus H-1" BMC Cancer, 2011, 11:1-14.
Souers, et al. "ABT-199, a potent and selective BCL-2 inhibitor, achieves antitumor activity while sparing platelets" Nature Medicine, 2012, 19:202-208.
Su, et al. "ABT-737 Synergizes with Arsenic Trioxide to Induce Apoptosis of Gastric Carcinoma Cells In Vitro and In Vivo" The Journal of International Medical Research, 2012, 20:1251-1264.

*Primary Examiner* — Bao Q Li
(74) *Attorney, Agent, or Firm* — Duane Morris LLP; Thomas J. Kowalski; Deborah L. Lu

(57) ABSTRACT

Described is a pharmaceutical composition comprising (a) a parvovirus and (b) an Bcl-2 inhibitor and the use of said composition for treatment of cancer, e.g., a solid tumor. Preferred inhibitors are the BH3 mimetics ABT-737 and ABT-199.

3 Claims, 33 Drawing Sheets

FIG 4A
Astrocytes
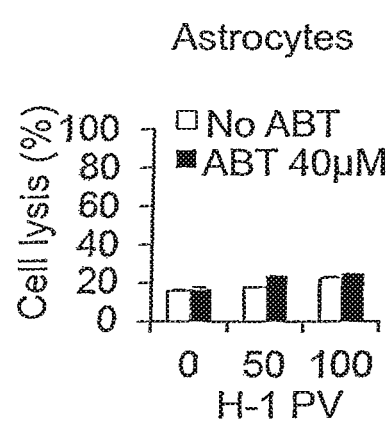
FIG 4B
POF
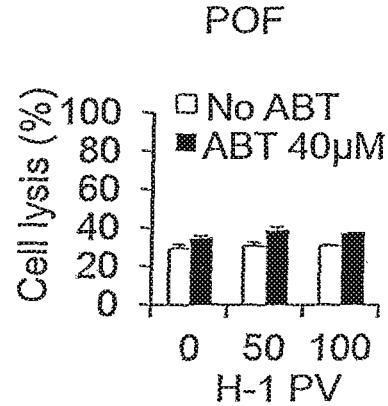
Melanocytes
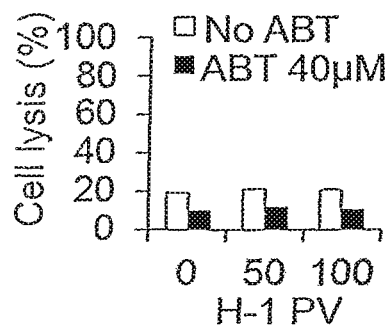
HFF
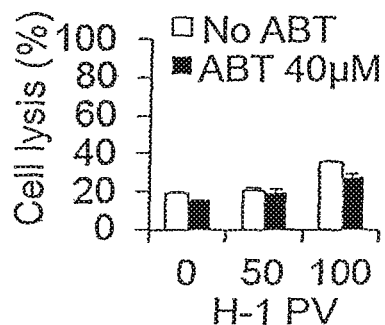
FIG 4C
FIG 4D

ABT-199

CANCER THERAPY WITH A PARVOVIRUS COMBINED WITH A BCL-2 INHIBITOR

RELATED APPLICATIONS AND INCORPORATION BY REFERENCE

This application is continuation of U.S. application Ser. No. 14/960,608 filed Dec. 7, 2015, now pending, which is a continuation-in-part application of international patent application Serial No. PCT/EP2014/002001 filed Jul. 22, 2014, which published as PCT Publication No. WO 2015/010782 A1 on Jan. 29, 2015, which claims benefit of European patent application Serial No. 13003664.3 filed Jul. 22, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a pharmaceutical composition comprising (a) a parvovirus and (b) a Bcl-2 inhibitor and the use of said composition for treatment of cancer, e.g., a solid tumor.

BACKGROUND OF THE INVENTION

Cancer is the second leading cause of death worldwide. It has been estimated that half of men and one third of women will be diagnosed with some form of cancer during their lifespan. Moreover, because cancer is predominantly a disease of aging, the number of cancer deaths worldwide is predicted to increase about 45% from 2007 to 2030 (from 7.9 million to 11.5 million deaths) due to the increase proportion of elderly people (WHO estimates, 2008). Cancer is also the most costly disease. The latest estimates from the National Cancer Institute showed that the overall economic cost of cancer in the U.S. in 2007 was $226.8 billion and unless more successful preventive interventions, early detection and more efficient treatments will be developed, this already huge economic burden is expected to further grow during the next two decades. Despite significant progresses in the prevention, detection, diagnosis and treatment of many forms of cancer, which is testified by an increase of the percentage of 5-years cancer survivals in U.S. and in Europe over the last thirty years, some tumour types, such as pancreatic, liver, lung, brain remain orphan of effective treatments calling for the development of new therapeutic options. Oncolytic viruses, which exploit cancer-specific vulnerabilities to kill cancer cells while sparing normal cells are fast emerging as promising tools for fighting cancer (Breitbach et al, 2011; Russell et al, 2012). No less than twelve different oncolytic viruses are currently undergoing phase I-III clinical trials against various malignancies (Russell et al, 2012) used alone or in combination with other anticancer agents. Among them, the oncolytic rat parvovirus H-1PV is currently evaluated for safety and first signs of efficacy in a phase I/IIa clinical trial in patients having recurrent glioblastoma multiforme (GBM) (Geletneky et al, 2012).

H-1PV is a small (~25 nm in diameter), non-enveloped icosahedral particle containing a 5.1 kb long single-stranded DNA genome (Cotmore & Tattersall, 2007). The genomic organization of H-1PV consists of two transcriptional units under the control of two promoters, the P4 early promoter and P38 late promoter. P4 regulates the expression of the gene encoding for the non-structural (NS) proteins (NS1 and NS2) and the P38 the one encoding for the capsid (VP) proteins (VP1, VP2, VP3) (Cotmore & Tattersall, 2007). The virus multiplies preferentially in fast dividing cancer cells. This onco-selectivity is not based on a better uptake of the virus by cancerous cells, but rather is due to the fact that cancer cells overexpress factors such as cyclin A, E2F, or CREB/ATF required for virus DNA replication. Furthermore, cancer cells are often defective in their ability to mount an efficient antiviral immune response favouring viral multiplication (Nuesch et al, 2012). The virus is known to activate multiple cell death pathways. Depending on cell type and growing conditions, H-1PV may induce apoptosis (Hristov et al, 2010; Ohshima et al, 1998; Rayet et al, 1998; Ueno et al, 2001), necrosis (Ran et al, 1999), or cathepsin B-dependent cell death (Di Piazza et al, 2007). The virus was able to induce oncolysis even in cancer cells resistant to TRAIL (Tumor Necrosis Factor Related Apoptosis Inducing Ligand), cisplatin and even when Bcl-2 was overexpressed (di Piazza et al., 2007). The latter results suggest that Bcl-2 is not a negative modulator of parvovirus cytotoxicity. Cancer therapy using a parvovirus and its combination with chemotherapy or an HDAC inhibitor has been recently described (WO 2009/083232 A1; WO 2011/113600 A1).

The major non-structural protein NS1 is the master regulator of virus DNA replication, viral gene expression and cytotoxicity. The sole expression of NS1, similarly to the entire virus, is sufficient to induce cell cycle arrest, apoptosis and cell lysis via accumulation of reactive oxygen species and DNA damage (Hristov et al, 2010). As results of its oncolytic activities, the virus has been shown to possess oncosuppressive properties demonstrated in a number of animal models which lay the basis for the launch of the clinical trial against GBM (Geletneky et al, 2012).

However, in the framework of cancer therapy as also observed with other anticancer agents, there is a risk that some cancer cells may be resistant or acquire resistance to H-1PV cytotoxicity leading to tumour relapse. Therefore, there is a need for the rational design of combination therapy, involving H-1PV and other anticancer agents, which complement each other and enhance their individual therapeutic effects without increasing unwanted side-effects for normal tissues.

Citation or identification of any document in this application is not an admission that such document is available as prior art to the present invention.

SUMMARY OF THE INVENTION

Therefore, it is the object of the present invention to provide means for an improved parvovirus-based therapy.

According to the invention this is achieved by the subject matters defined in the claims.

In the study resulting in the present invention it was asked whether the Bcl-2 inhibitors ABT-737 or ABT-199 synergize with H-1PV in killing cancer cells. It was shown that sub-lethal doses of ABT-737 (and ABT-199) potentiate the oncolytic activity of H-1PV in a synergistic manner in 25 human cell lines derived from a broad range of solid tumours such as gliomas (n=11), pancreatic carcinomas (n=3), cervical carcinomas (n=3), lung (n=3), head and neck (n=3), breast (n=1), and colon (n=1) cancer, while preserving the safety profile of the virus for normal non-transformed primary cells. Surprisingly, strong synergistic effects were also observed in cancer cell lines notoriously resistant to parvovirus cytotoxicity. Remarkably, the H-1PV/ABT-737 co-treatment was also effective against tumour initiating stem-cell cultures derived from brain and cervical cancers (n=5). In H-1PV/ABT-737 co-treated glioma-derived cell lines, an increased induction of apoptosis characterized by (mitochondrial membrane permilization (MMP) and activation of caspase 3 and 7 could also be demonstrated.

Altered response to apoptotic signals is a hallmark of cancer (Hanahan & Weinberg, 2011). Apoptosis occurs through the activation of two different, yet cross-talking, pathways: the extrinsic pathway, initiated by pro-apoptotic ligands such as Apo2/TRAIL, which activate cell surface death receptors, and the intrinsic pathway, which is triggered by intracellular stress signals and results in mitochondrial outer membrane permeabilization (MMP) followed by release of cytochrome C from the mitochondria to the cytosol and finally activation of caspases. The B-cell lymphoma 2 (Bcl-2) family members play a central role in the regulation of apoptosis controlling the integrity of the outer mitochondrial membrane (Youle & Strasser, 2008). Twenty-five members of the Bcl-2 protein family have been identified so far. Depending on their effect on the apoptotic pathway and the number of Bcl-2 homology domains, they are subdivided into anti-apoptotic proteins (Bcl-2, Bcl-$X_L$, Bcl-w, Mcl-1, Bfl-1), pro-apoptotic BH3-only proteins (Bim, Bad, Bid, Bik etc.) and Bax-like pro-apoptotic proteins (Bax, Bak and Bok) (Bajwa et al, 2012). The balance between pro-apoptotic and anti-apoptotic proteins determines the fate of a cell. If the number of pro-apoptotic proteins cannot be neutralized by anti-apoptotic proteins, Bak and Bax oligomerize and form large-conductance pores in the mitochondria membrane resulting in the induction of apoptosis. Anti-apoptotic Bcl-2 proteins are often overexpressed in a variety of cancer types, including lymphoma, lung, liver, colorectal, ovarian, prostate, brain and breast cancers (Andersen et al, 2005) and are frequently associated with tumour initiation, progression and resistance to conventional chemotherapeutic drugs (Bajwa et al, 2012). Therefore, many efforts have been directed in trying to antagonize the activity of these anti-apoptotic proteins. One of these strategies is the use of small selective molecules such as the BH3 mimetics ABT-737 and ABT-199.

Like BH3-only proteins, BH3 mimetics inhibit anti-apoptotic Bcl-2 family members by binding to their hydrophobic groove (Cragg et al, 2009). Liberation of activating BH3-only proteins induces activation of Bax and Bak and triggers apoptosis. The BH3 mimetic ABT-737 was discovered by Oltersdorf and colleagues. It binds with high affinity (Ki≤1 nM) to Bcl-2, Bcl-$X_L$ and Bcl-w (Oltersdorf et al, 2005) and displaces BH3-only protein like BIM from Bcl-2 (Del Gaizo Moore et al, 2007). In vitro it was shown to induce apoptosis as a single agent in leukemia and lymphoma cells, in multiple myeloma and small-cell lung cancer derived cell lines (Vogler et al, 2009). ABT-737 treatment led to complete regression of small-cell lung carcinoma in xenograft mouse models (Oltersdorf et al, 2005). In addition ABT-737 was shown to synergistically enhance cytotoxicity of the anticancer drug paclitaxel in non-small cell lung carcinoma (Oltersdorf et al, 2005) as well as of vincristine and etoposide in glioblastoma cells (Tagscherer et al, 2008). Non malignant peripheral blood mononuclear cells (PBMCs) are not sensitive to ABT-737 as the half maximal effective concentration (EC50) was determined to be higher than 1000 nM (Del Gaizo Moore et al, 2007). Currently, ABT-263 an orally available derivative of ABT-737 is tested in phase II clinical trials against lymphoid malignancies, non-Hodgkin's lymphoma, chronic lymphoid leukemia, follicular lymphoma, mantle cell lymphoma and peripheral T-cell lymphoma (ClinicalTrials.gov). However, concern about thrombocytopenia has limited the introduction of ABT-737 and ABT-263 into clinical trials of acute leukemias, despite their strong anticancer activity. This is most likely due to an on-target toxicity resulting from the dependence of platelets on BCL-$X_L$ (Davids & Letai, 2012). Recently, Souers and colleagues generated the highly selective Bcl-2 inhibitor ABT-199 by modifying ABT-263, a closely related orally available analogue of ABT-737. ABT-199 selectively binds with high affinity to Bcl-2 ($K_i$≤0.01 nM), but not to Bcl-$X_L$ ($K_i$=48 nM) and Bcl-w ($K_i$=245 nM) (Souers et al, 2013). In vivo it was shown to inhibit tumor growth in several human hematologic tumour xenograft models and in contrast to ABT-737, it spares human platelets with less side-effects (Souers et al, 2013). Recently, it has been reported that Bcl-2 inhibitor treatment sensitizes chronic lymphocytic leukemia (CLL) derived cell lines to Vesicular Stomatitis Virus (VSV) oncolysis and that apoptosis resistance may be overcome (Samuel et al., 2010; Samuel et al, 2013).

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 4A-D: ABT-737 and H-1PV are not harmful for normal primary cells under treatment conditions of the present invention The safety profile of H-1PV/ABT-737 co-treatment was assessed in human astrocytes (a), primary oral fibroblasts (POF, b), melanocytes (c) and human foreskin fibroblasts (HFF, d). 4,000 cells/well were seeded in 96-well plates and after 24 hours treated or not with indicated concentrations of H-1PV (MOI: pfu/cell) and/or 40 µM ABT-737 (ABT). 96 hours after infection, cell lysis was analyzed by LDH assay as described in the materials and methods section. Columns represent the mean values from 3 replicates with relative standard deviation bars.

The occurrence of DNA fragmentation (sub-G1 cell population) in response to treatment was assessed by propidium iodide staining and flow cytometry in eight human glioma cell lines (a-h). $2.5 \times 10^5$ cells/well (or $6.25 \times 10^4$ cells/well for NCH37 and NCH125) were seeded in 6-well plates and after 24 hours treated or not with indicated concentrations of H-1PV and/or ABT-737 (ABT). 48-96 hours after infection, cells were stained and analyzed as described in the materials and methods section. Representative histogram plots are shown in the upper panel. Graph in the lower panel shows the results of a typical experiment performed in triplicate. Columns represent the mean values with relative standard deviation bars (lower panel).

FIGS. 6A-D: ABT-737 and H-1PV induce mitochondrial membrane permeabilization (MMP)

The effect of H-1PV/ABT-737 co-treatment on MMP (a hallmark of apoptosis) was assessed by Mitotracker Red staining and flow cytometry in four human glioma cell lines (a-d). $2.5 \times 10^5$ cells/well (or $6.25 \times 10^4$ cells/well for NCH125) were seeded in 6-well plates and after 24 hours treated or not with H-1PV and/or ABT-737 at the indicated concentrations. 48-96 hours after infection, cells were stained with Mitotracker Red, harvested and analyzed by flow cytometry. The percentage of cells with MMP, was determined using the CellQuest Software. In the upper panel representative histogram plots are shown for each condition. In the lower panel the results of a typical experiment performed in triplicates are shown. Columns represent the mean values with relative standard deviation bars.

FIGS. 7A-H: ABT-737 and H-1PV induce apoptosis via caspase-3/7

Induction of apoptosis was assessed by analyzing active caspase 3 and 7 (cleaved forms) in eight human glioma cell lines using the CellEvent® Caspase-3/7 Green Detection Reagent (a-h). 4,000 cells/well were seeded on 10-well microscope slides and after 24 hours treated or not with H-1PV and/or ABT-737 at the indicated concentrations. 48 hours after infection, cells were stained with the Caspase-3/7 Green Detection Reagent and fixed. Nuclei were visualized by DAPI staining. The fluorescence signal was detected by microscopy using the blue and green channel at 20× magnification. Representative images are shown.

Figure 8:
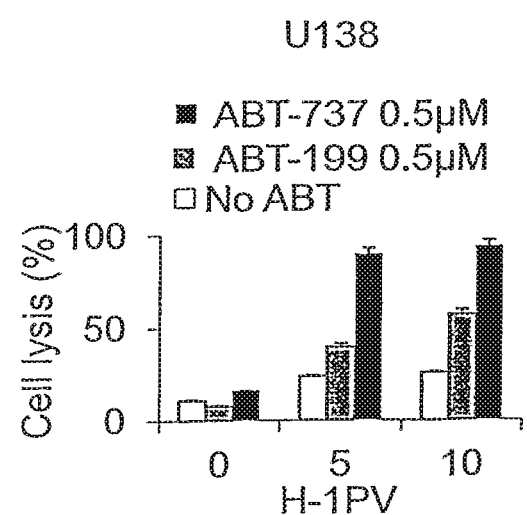

FIG. 8: ABT-199 potentiates H-1PV induced oncolysis

LDH assay: The efficiency of ABT-737 and ABT-199 in combination with H-1PV was compared in the human glioblastoma cell line U138. 4,000 cells/well were seeded in 96-well plates and after 24 hours treated or not with H-1PV and/or ABT-737 and/or ABT-199 at the indicated concentrations. 72 hours after infection, percentage of cells undergoing lysis was measured by LDH assay. Columns represent mean values from 3 replicates with relative standard deviation bars.

Figure 9:
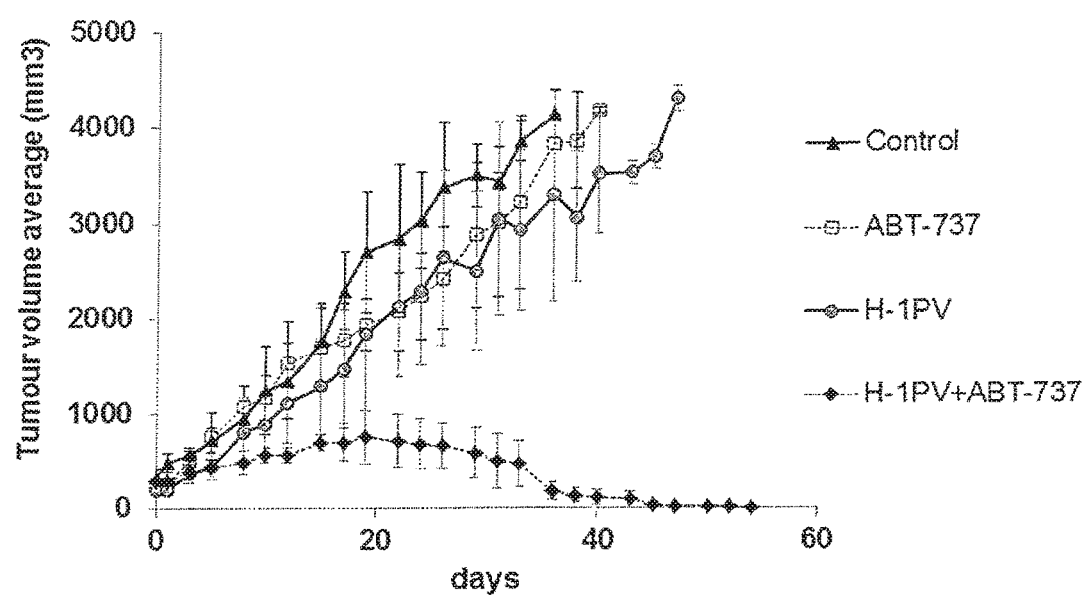

FIG. 9: H-1PV/ABT-737 co-treatment leads to complete regression of AsPC-1 xenografts $5 \times 10^6$ AsPC-1 cells were subcutaneously injected in the right flank of 5 week-old female nude rats. After 1 week (when tumour reached the volume of 200-400 mm$^3$), tumour-bearing animals were randomized in to four groups (n=8). Groups were treated either with PBS (control), ABT-737 (50 mg/kg, given every second day for the first 14 days), H-1PV (total dose of 2.5 $10^8$ pfu/animal, fractionated in 4 intratumoral administrations), or a combination of both agents. Tumour volume was measured with a digital calliper on the days indicated and calculated according to the formula: volume (cm$^3$)=width$^2$× length/2. Rats were sacrificed when the tumour mass reached 4000 mm$^3$, in keeping with animal welfare regulations. Data shown represents the average values with standard deviation bars.

Figure 10:
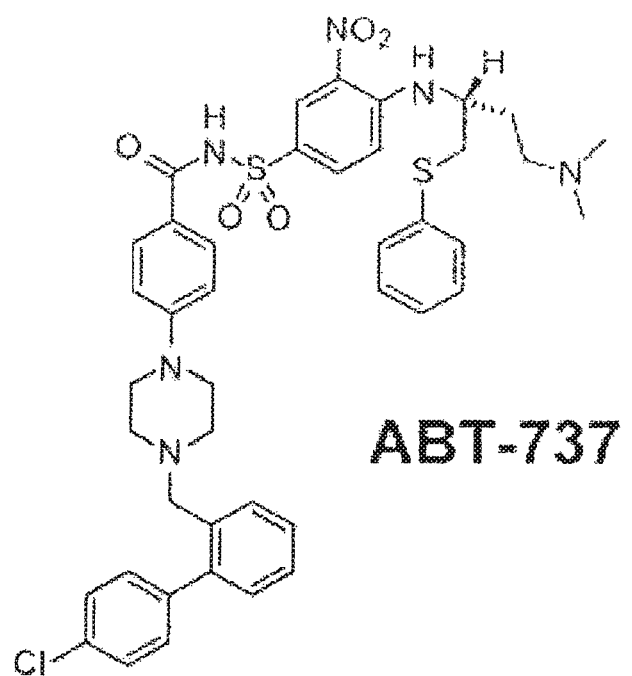

FIG. 10: Structure of ABT-737

Figure 11:
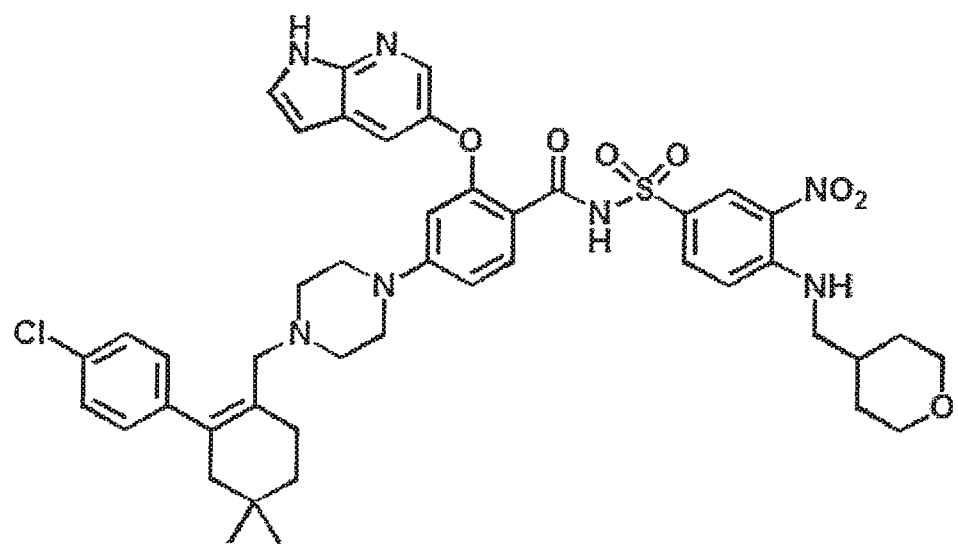

FIG. 11: Structure of ABT-199

DETAILED DESCRIPTION OF THE INVENTION

The present invention provides a pharmaceutical composition containing (a) a parvovirus and (b) a Bcl-2 inhibitor.

Preferably, in said pharmaceutical composition the parvovirus and the Bcl-2 inhibitor are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art.

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical, intratumoral or intradermal administration. The route of administration, of course, depends on the kind of therapy and the kind of compounds contained in the pharmaceutical composition. The dosage regimen of the parvovirus and the Bcl-2 inhibitor is readily determinable within the skill of the art, by the attending physician based an patient data, observations and other clinical factors, including for example the patient's size, body surface area, age, sex, the particular parvovirus, the particular inhibitor etc. to be administered, the time and route of administration, the tumor type and characteristics, general health of the patient, and other drug therapies to which the patient is being subjected.

If the parvovirus in the combination with Bcl-2 inhibitors according to the invention comprises infectious virus particles with the ability to penetrate through the blood-brain barrier, treatment can be performed or at least initiated by intravenous injection of the virus. However, a preferred route of administration is intratumoral administration.

Since long-term intravenous treatment is susceptible to becoming inefficient as a result of the formation of neutralizing antibodies to the virus, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the parvovirus (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus composition to be injected locally at various times without further surgical intervention. The parvovirus or derived vectors can also be injected into the tumor by stereotactic surgical techniques or by neuronavigation targeting techniques.

Administration of the parvovirus can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvovirus composition is from an implanted article constructed and arranged to dispense the parvovirus to the desired cancer tissue. For example, wafers can be employed that have been impregnated with the parvovirus, e.g., parvovirus H-1, wherein the wafer is attached to the edges of the resection cavity at the conclusion of surgical tumor removal. Multiple wafers can be employed in such therapeutic intervention. Cells that actively produce the parvovirus, e.g., parvovirus H-1, or H-1 based vectors, can be injected into the tumor or into the tumoral cavity after tumor removal.

The combined therapy according to the invention is useful for the therapeutic treatment of cancer, in particular (but not exclusively) brain tumor, pancreatic carcinoma, cervical carcinoma, lung cancer, head and neck cancer, breast cancer or colon cancer and can significantly improve the prognosis of said diseases. It can also allow the clinical use of the virus and/or bcl-2 inhibitor(s) at lower therapeutic doses preserving or even enhancing anticancer efficacy while increasing safety and reducing and/or avoiding side effects. In view of the strong synergistic effect between the parvovirus and the Bcl-2 inhibitor it is possible to foresee the reduction of the therapeutic doses, e.g. half or a third of the previously used single component doses are preserving the desired therapeutic effect. In view of the reduced doses (severe) side effects may be reduced or even avoided.

Parvovirus infection effects killing of tumor cells but does not harm normal cells and such infection can, for example, be carried out by intracerebral use of a suitable parvovirus, e.g., parvovirus H-1, or a related virus or vectors based on such viruses, to effect tumor-specific therapy without adverse neurological or other side effects.

The present invention also relates to the use of (a) a parvovirus and (b) a Bcl-2 inhibitor for the preparation of (a) pharmaceutical composition(s) for the treatment of cancer.

The mode of administration of (a) and (b) may be simultaneously or sequentially, wherein, preferably, (a) and (b) are sequentially (or separately) administered. This means that (a) and (b) may be provided in a single unit dosage form for being taken together or as separate entities (e.g. in separate containers) to be administered simultaneously or with a certain time difference. This time difference may be between 1 hour and 1 week, preferably between 12 hours and 3 days. In addition, it is possible to administer the parvovirus via another administration way than the Bcl-2 inhibitor. In this regard it may be advantageous to administer either the parvovirus or the Bcl-2 inhibitor intratumoraly and the other systemically or orally. In a particular preferred embodiment the parvovirus is administered intratumoraly and the Bcl-2 inhibitor intravenously or orally.

In one preferred embodiment of the present invention, the combination of agents is utilized in the treatment of solid tumours. Examples are brain tumour, pancreatic carcinoma, cervical carcinoma, lung cancer, head and neck cancer, breast cancer or colon cancer. In a preferred embodiment these tumours are resistant to parvovirus toxicity. A particular advantage of the pharmaceutical composition of the present invention is that even cancer initiating stem cells can be successfully treated.

In an embodiment of the present invention, the parvovirus of the composition includes parvovirus H-1 (H-1PV) or a related parvovirus such as LuIII, Mouse minute virus (MMV), Mouse parvovirus (MPV), Rat minute virus (RMV), Rat parvovirus (RPV) or Rat virus (RV).

Patients treatable by the combination of agents according to the invention include humans as well as non-human animals. Examples of the latter include, without limitation, animals such as cows, sheep, pigs, horses, dogs, and cats.

Bcl-2 inhibitors useful for the purposes of the present invention include all compounds that (a) increase the anticancer potential of parvovirus, preferably without side-effects for normal cells, and (b) inhibit anti-apoptotic proteins like Bcl-2, Bcl-$X_L$, Bcl-w, Mcl-1, Bfl-1 pBcl-2 and/or are mimetics of the pro-apoptotic BH3-only proteins (bim, Bad, Bid, Bik, etc.) or Bax-like pro-apoptotic proteins (Bax, Bak, Bok). The administration of a Bcl-2 inhibitor can be accomplished in a variety of ways (see above) including systemically by the parenteral and enteral routes. Preferably, the parvovirus and the Bcl-2 inhibitor are administered as separate compounds. Concomitant treatment with the two agents is also possible.

Examples of Bcl-2 inhibitors suitable for the combined therapy include ABT-263, Obatoclax mesylate (GX15070), TW-37, HA14-1, Apogossypolone (ApoG2), BAM7, Sabutoclax, AT101 and BM-1074. Particularly preferred is the use of a BH3 mimetic small molecule inhibitor, preferably ABT-737 (available from Selleck Chemicals LLC, Houston, Tex.; FIG. 10) and ABT-199 (available from Active Biochemicals, Maplewood, N.J.; FIG. 11).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Materials and Methods (A) Cell Lines and Culture

The human glioblastoma-derived cell lines U373, U251, T98G, A172 and U87 were a kind gift of Dr. Iris Augustin (DKFZ, Heidelberg, Germany). U138 and U343 were provided by Tumorbank (DKFZ, Heidelberg, Germany). The glioblastoma-derived cell lines NCH89, NCH82, NCH125 and the gliosarcoma-derived cell line NCH37 were prepared and characterized at the Department of Neurosurgery (Heidelberg, Germany). The HeLa and SiHa cervical carcinoma (CC) cell lines were kindly provided by Prof. Dr. Angel Alonso (DKFZ, Heidelberg, Germany). The CC-derived cell line CaSki and the pancreatic ductal adenocarcinoma (PDAC)-derived cell lines MIA PaCa-2, T3M-4 and AsPC-1 were purchased from ATCC (LGC Standards GmBH, Wesel, Germany). The head and neck squamous cell carcinoma (HNSCC) cell lines HNC97, Ca127, 211MC and human primary oral fibroblasts (POF) and human foreskin fibroblasts (HFF) were a kind gift of Dr. Massimo Tommasino (IARC, Lyon, France). The lung cancer (LC) cell lines EKVX, Hop92, H322M, the colon colorectal carcinoma cell line HCT-116 and the breast cancer cell line Hs578T were purchased from the National Cancer Institute (NCI) (Bethesda, Md.). The glioma-derived cell lines LN229, LN308 and the glioma-initiating cell (GIC) lines T269, S24 and T325 were kindly provided by Prof. W. Wick (Department of Neurooncology, University of Heidelberg, Germany).

Stem cell-like U87 cells were isolated from the U87 cell line as described by Yu and colleagues (Yu et al, 2008). Spheroids were generated from the HeLa cell line according to the method described by Chen and colleagues (Chen et al, 2011). Human melanocytes were purchased from Invitrogen (Carlsbad, Calif.) and astrocytes from ScienCell Research Laboratories (San Diego, Calif.).

The glioma-derived cell lines were cultured in Dulbecco's modified Eagle's medium (DMEM) with high glucose concentration (Gibco, Life Technologies, Darmstadt, Germany). The HeLa, CaSki, SiHa, AsPC-1, HNC-97, 211MC, Ca127 and HFF cell lines were grown in DMEM (SIGMA-Aldrich, Munich, Germany). T3M-4, MIA PaCa-2, H322M, HOP-92, EKVX, HCT-116 and Hs578T were cultured in Roswell Park Memorial Institute medium 1640 (RPMI, Invitrogen, Karlsruhe, Germany). All media were supplemented with 10% heat-inactivated fetal bovine serum (FBS, PAA, Cölbe, Germany) and 2 mM L-glutamine (Gibco). Except for glioma cells, the media additionally contained 100 U/ml of penicillin (Gibco) and 100 µg/ml of streptomycin (Gibco). The glioma-derived cancer stem cell (CSC) cultures T269, S24, T325 and U87 were grown in DMEM/F-12 (Gibco), supplemented with 20% BIT-100 (Provitro, Berlin, Germany), 100 U/ml penicillin and 100 µg/ml streptomycin (Gibco) and 20 ng/ml human fibroblast growth factor (FGF-2) and 20 ng/ml epidermal growth factor (EGF) (Biochrom AG, Berlin, Germany). Spheroid HeLa cells were cultured in serum-free Quantum 263 medium (Biochrom AG), supplemented with 10 ng/ml FGF-2 and 10 ng/ml EGF. Melanocytes were cultured in Medium 254 with Human Melanocyte Growth Supplement (HMGS) (Invitrogen, Darmstadt, Germany). Astrocytes were cultured in Astrocyte Medium (Gibco). POF were cultured in DMEM without L-glutamine and phenol red. All cells were grown at 37° C., 5% CO2, 95% humidity and routinely checked for mycoplasma contamination.

(B) Virus Production

Wild-type H-1PV was produced in NB324K cells by Barbara Leuchs and purified in iodixanol gradients as previously described (Wrzesinski et al, 2003). Virus titers were determined by plaque assays (Daeffler et al, 2003). H-1PV was UV-treated with a total dose of 50 ml/cm$^2$ as described by Morita and colleagues (Morita et al, 2003).

(C) Lactate Dehydrogenase (LDH) Assay

H-1PV cytotoxicity was evaluated by quantification of the enzyme lactate dehydrogenase (LDH), which is released from cells due to loss of membrane integrity (lysis). The assay was performed using the CytoTox 96® Non-Radioactive Cytotoxicity Assay Kit according to the manufacturer's instructions (Promega, Heidelberg, Germany).

Cells were seeded into 96-well plates usually at the density of 4,000 cells/well in 50 µl of their respective culture media supplemented with 10% FBS. Taking into account the different growth rates of some cell lines, 2,000 cells were seeded for T3M-4 and HeLa cells and 10,000 cells for the cancer stem cell cultures. After 24 hours, 50 µl of FBS-free medium with or without H-1PV and/or ABT-737 (Selleck Chemicals LLC, Houston, Tex.) were added to the cells at the concentrations indicated in Table 1.

TABLE 1

CELL LINES AND TREATMENT CONDITIONS

| Tumor origin | Cell lines | H-1PV (MOI) | ABT-737 (µM) |
|---|---|---|---|
| Brain | U373 | 25, 50, 75, 100 | 2.5 |
| Glioblastoma | LN308 | 1, 2.5, 10, 25 | 0.1 |
| | U251 | 5, 10, 25, 50 | 2.5 |
| | T98G | 1, 5, 10, 25 | 1 |
| | U138 | 1, 2.5, 5, 10 | 0.5 |
| | U343 | 1, 2.5, 5, 10 | 2.5 |
| | A172 | 2.5, 5, 10, 20 | 1.25 |
| | LN229 | 1, 2.5, 10, 25 | 0.1 |
| | U87 | 1, 2.5, 5, 10 | 5 |
| | NCH125 | 1, 2.5, 5, 10 | 1 |
| Gliosarcoma | NCH37 | 1, 2.5, 5, 10 | 1 |
| Glioma-initiating stem cells | T269 | 1, 2.5, 5, 10 | 0.1 |
| | S24 | 1, 5, 10, 25 | 0.1 |
| | T325 | 1, 2.5, 5, 10 | 0.1 |
| | U87 (stem) | 1, 2.5, 5, 10 | 1 |
| Pancreas | MIA PaCa-2 | 0.5, 1, 5, 10 | 2.5 |
| | T3M-4 | 5, 10, 25, 50 | 0.625 |
| | AsPC-I | 25, 50, 100, 200 | 0.625 |
| Cervix | HeLa | 0.1, 0.5, 0.75, 1 | 1 |
| | CaSki | 1, 2.5, 5, 10 | 0.3125 |
| | SiHa | 1, 2.5, 5, 10 | 0.625 |
| Stem-like cells | HeLa (stem) | 0.005, 0.01, 0.05, 0.1 | 1 |
| Lung | H322M | 1, 5, 10, 20 | 0.5 |
| | HOP92 | 1, 2.5, 5, 7.5 | 0.5 |
| | EKVX | 1, 2.5, 5, 7.5 | 0.5 |
| Head and Neck | HNC97 | 1, 2.5, 5, 10 | 1.25 |
| | 211MC | 5, 10, 20, 40 | 1.25 |
| | Cal27 | 10, 25, 50, 100 | 2.5 |
| Colon | HCT-116 | 5, 10, 25, 50 | 2.5 |
| Breast | Hs578T | 0.5, 1, 2.5, 5 | 0.1 |

Melanocytes, astrocytes, HFF and POF were infected with H-1PV at the high multiplicity of infection (MOI, plaque forming unit (pfu) per cell) of 50 and 100 pfu/cell in presence or absence of 40 µM ABT-737. The LDH assay was performed as stated above except for a prolonged incubation time of 96 hours instead of 72 hours after the infection.

For direct comparison of the efficiency of ABT-737 and ABT-199, the glioblastoma cell line U138 was infected with H-1PV at a MOI of 5 and 10 pfu/cell and treated or not with 0.5 µM ABT-737 or ABT-199 (Active Biochemicals, Maplewood, N.J.).

For each condition tested, 7 replicates were prepared of which 3 were used for calculating the total cell lysis in the presence of detergent. One line of the plate was left without cells for background calculation. After 72 hours at 37° C., the cells were processed for the LDH assay as previously described (El-Andaloussi et al, 2012).

Briefly, 10 µl of 10× lysis buffer [9% (v/v) Triton X-100 (AppliChem, Darmstadt, Germany) in phosphate buffered saline (PBS)] were added per well in three lines of the plate, which served as 100% cell lysis control. 10 µl of PBS were added to the other lines. When the cell lysis was completed, 30 µl of the supernatant of each well were transferred to a fresh 96-well plate. 30 µl of the substrate mix provided by the kit was added to each well. The plate was protected from light and incubated at room temperature for 30 min before reaction was stopped by adding 30 µl of the stop solution provided by the kit. The absorbance was measured at a wavelength of 492 nm using the Multiscan ELISA Reader. The amount of color that is formed by conversion of the tetrazolium salt into a red formazan product is proportional to the number of lysed cells. For each condition we calculated the average of the three wells incubated (A) or not (B) with lysis buffer. The average value measured in the wells without cells (background) was subtracted from the values obtained in the wells with the cells. The percentage of total lysis was calculated using the following formula:

$$\text{Cell lysis [\%]} = (A-\text{background})/(B-\text{background}) \times 100$$

(D) Determination of the Sub-G1 Apoptotic Population by Flow Cytometry

Propidium iodide staining was performed, in order to detect apoptotic cells after treatment. The dye intercalates in the DNA, where it can be measured by flow cytometry. The fluorescence emission is proportional to the DNA content in the cells. Apoptotic cells are characterized by nuclear DNA fragmentation and can be identified by lower fluorescence emission (sub-G1 apoptotic cell population) (Riccardi & Nicoletti, 2006).

Glioma cells (U373, U251, U138, U343, A172, NCH37, U87, NCH125) were seeded in 6-well plates at the density of $2.5 \times 10^5$ cells/well in 3 ml of cultural medium with the exception of NCH37 and NCH125 cells that were seeded at the density of $6.25 \times 10^4$ cells/well. 24 hours after seeding, the cells were infected or not with H-1PV at a MOI of 0.5-7.5 pfu/cell and/or treated with 0.25-5 µM ABT-737. H-1PV and ABT-737 were diluted in DMEM with 10% FBS and a final volume of 200 µl was added to the wells. All conditions were tested in triplicates.

After 48 (U251, U138, A172, U87, NCH125), 72 (U373) or 96 (U343, NCH37) hours, from infection, supernatant and cells (harvested by trypsinization) were collected and washed with PBS. After centrifugation, the cell pellet was resuspended in 500 µl of PBS and cells were fixed with 4.5 ml of ice-cold 70% ethanol added dropwise. Cells were then stored at −20° C. for up to 24 h. Before staining, cells were centrifuged and washed once with PBS. Cells were then resuspended in 1 ml of DNA staining solution containing 20 µg/ml of propidium iodide (Sigma-Aldrich) and 200 µg/ml of RNase (Promega) and incubated for 30 minutes at room temperature in the dark. The cell suspension was filtered in a nylon net, and measured on a FACSCalibur (BD Biosciences, San Jose, Calif.). A minimum of 20,000 events were acquired and analyzed with the CellQuest Software (BD Biosciences). Propidium iodide was detected in the FL-2 channel. Untreated cells were used to set the gate for the apoptotic cell fraction, as they show the fluorescence emission of viable non-apoptotic cells. The percentage of the sub-G1 population was determined in each sample and the average was calculated from the triplicates.

(E) Evaluation of Mitochondrial Membrane Permeabilization (MMP)

The fluorescent dye MitoTracker® Red CMXRos (Molecular Probes, Invitrogen, Darmstadt, Germany) that stains mitochondria in live cells was used to measure the change in MMP. Due to the formation of pores in the mitochondrial membrane, apoptotic cells cannot retain the dye and show a lower fluorescent signal in flow cytometry analysis.

Glioma cells were seeded in 6-well plates at the density of $2.5 \times 10^5$ cells/well in 3 ml of cultural medium with the exception of NCH125 cells that were seeded at the density of $6.25 \times 10^4$ cells/well. After 24 hours, cells were infected or not with H-1PV at a MOI of 2.5 pfu/cell (U343 and NCH125) or 5 pfu/cell (U373) or 7.5 pfu/cell (U138) and treated or not with ABT-737 at a concentration of 0.5 µM (U373, U138, U343) or 1 µM (NCH125) or co-treated with both agents. After 48 (U138, NCH125) or 72 (U373) or 96 (U343) hours of incubation, medium was replaced with 1 ml of mitochondrial staining solution containing the dye MitoTracker® Red CMXRos (200 nM) in DMEM without supplements. After 1 hour staining at 37° C., the cells were harvested by trypsinization, washed once with PBS and finally resuspended in PBS. Cell suspension was analyzed with a FACSCalibur (BD Biosciences). At least 10,000 events were acquired and analyzed with the CellQuest Software (BD Biosciences). The average of cells undergoing MMP was calculated from three replicates.

(F) Detection of Active Cleaved Caspase-3/7 Forms

The cleavage of caspase-3/7 (a hallmark of apoptosis) after treatment with H-1PV and ABT-737 was analyzed by using the CellEvent® Caspase-3/7 Green Detection Reagent (Invitrogen, Darmstadt, Germany). Activation of caspase 3 or 7 in apoptotic cells leads to cleavage of a peptide sequence from the reagent, which releases a nucleic acid binding dye. When the dye binds to DNA, it produces a green fluorescence signal that can be detected by fluorescence microscopy.

Cells were seeded at the density of 4,000 cells/well on 10-well microscope slides. After 24 hours, cells were infected with H-1PV at a MOI of 1 pfu/cell (NCH37 and NCH125) or 5 pfu/cell (U373, U251, U138, A172, U87) or 10 pfu/cell (U343) in the presence or absence of 0.25 µM ABT-737 (U373) or 1 µM (NCH37, NCH125) or 1.25 µM (A172) or 2.5 µM (U251, U138, U343, U87). Untreated cells were used as a control. After 24 hours, cells were stained with 10 µM of the CellEvent® Caspase-3/7 Green Detection Reagent for 30 min. The cells were then washed with PBS and fixed with 4% paraformaldehyde (PFA). For nuclei staining commercial DAPI solution (Vector Laboratories, Lörrach, Germany) was added to the cells. After washing with PBS, cells were mounted with a cover slip and analyzed by a fluorescence microscope (Keyence, Neu-Isenburg, Germany) using the blue and green channel at 20× magnification.

Example 2

ABT-737 Potentiates the Oncolytic Activity of H-1PV in a Synergistic Manner

It is known that H-1PV can infect human cancer cell lines from different tissues and exerts cytotoxic activities. However, not all cell lines respond at the same level to virus cytotoxicity with some cell lines being very sensitive to the virus while others nearly resistant (El-Andaloussi et al, 2012). Therefore, it would be extremely important to find other anticancer agents that could cooperate with H-1PV in killing cancer cells while preserving the excellent safety profile of the virus. As the cancer cell often features defects in cell death pathways, e.g. overexpression of anti-apoptotic Bcl-2 family members such as Bcl-2, Bcl-$X_L$, Bcl-w and Mcl-1, we hypothesized that these defects may contribute to resistance to H-1PV cytotoxicity and explored whether the use of the Bcl-2 inhibitor ABT-737 in combination with H-1PV may restore apoptotic cell death in cancer cells and result in enhanced therapeutic effects.

Figure 1A:
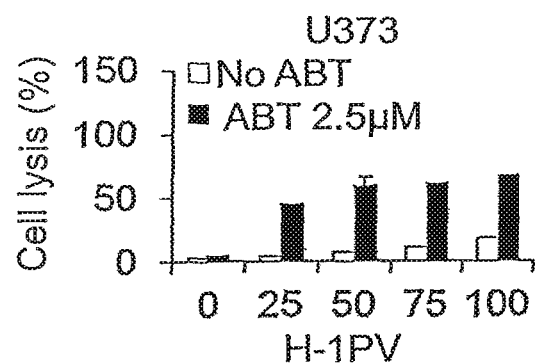
FIGS. 1A-K: ABT-737 enhances H-1PV induced cytotoxicity against human glioma cell lines in a synergistic manner LDH assays. The cytotoxicity of H-1PV/ABT-737 co-treatment was evaluated in 11 glioma cell lines (a-k) (the name of the cell lines is indicated at the top of graphs). 4,000 cells/well were seeded in 96-well plates and after 24 hours treated or not with the indicated concentrations of H-1PV (MOI: pfu/cell) and/or ABT-737 (ABT). 72 hours after infection, cell lysis was analyzed by LDH assay as described in the materials and methods section. Columns represent the mean values from 3 replicates with relative standard deviation bars.
Figure 1B:
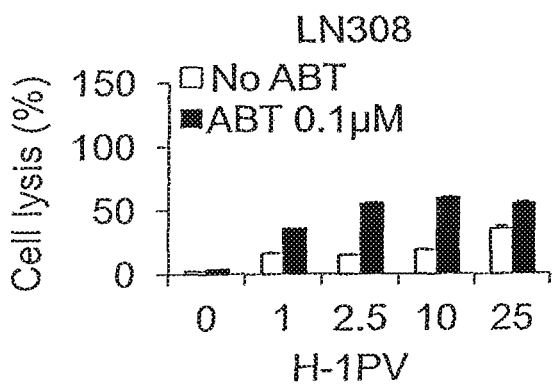
Figure 1C:
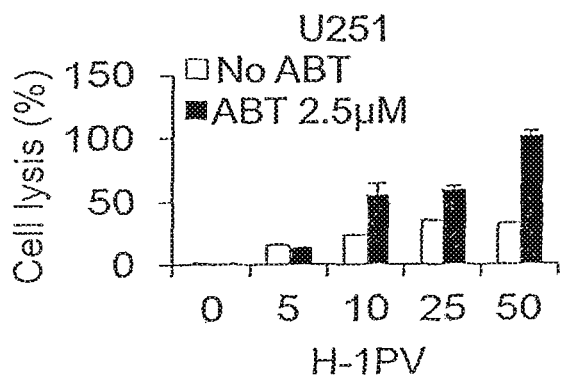
Figure 1D:
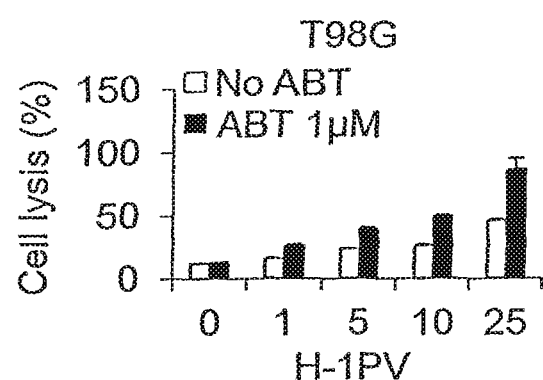
Figure 1E:
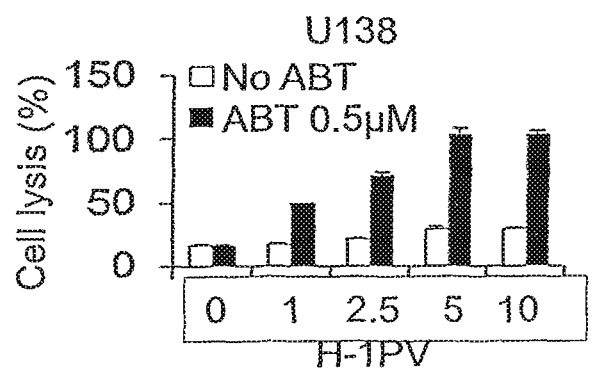
Figure 1F:
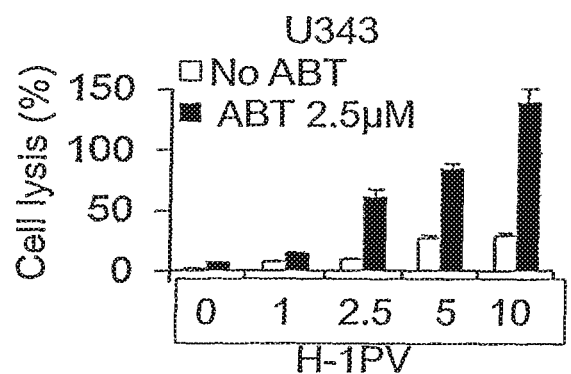
Figure 1G:
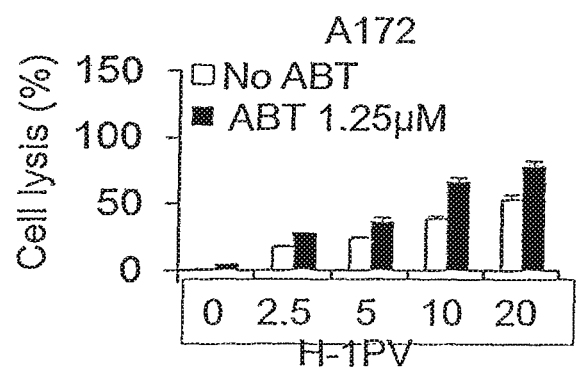
Figure 1H:
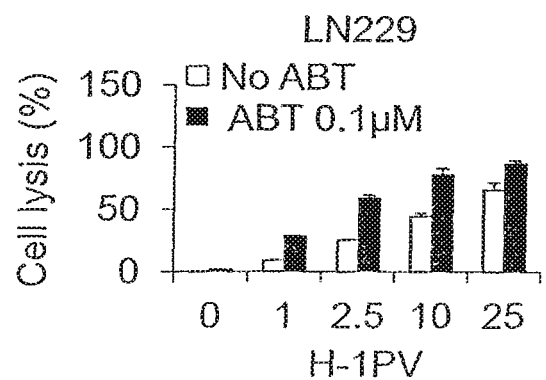
Figure 1I:
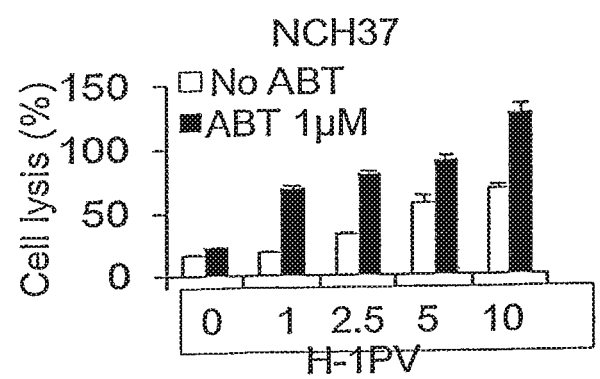
Figure 1J:
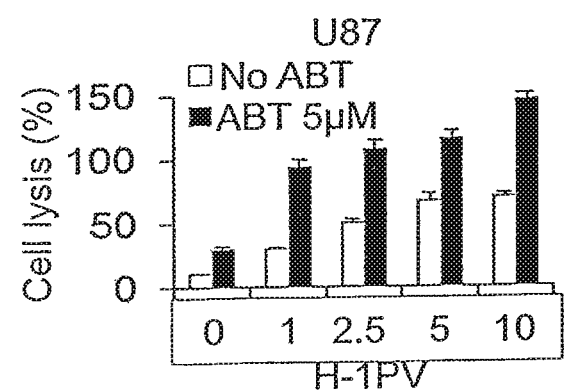
Figure 1K:
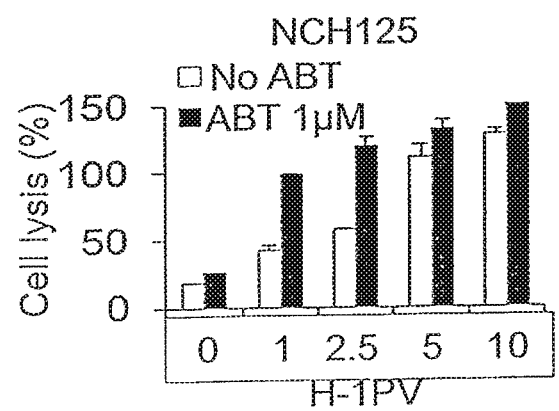
Figure 2A:
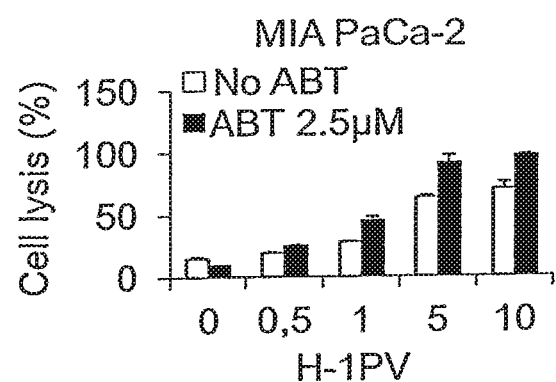
FIGS. 2A-N: ABT-737 enhances H-1PV induced cytotoxicity against human cell lines from various tumor entities in a synergistic manner LDH assays. The cytotoxicity of H-1PV/ABT-737 co-treatment was evaluated in 3 pancreatic ductal adenocarcinoma (a-c), 3 cervical carcinoma (d-f), 3 lung carcinoma (g-i), 3 head and neck squamous cell carcinoma (j-l), one colon colorectal carcinoma (m) and one breast cancer (n) cell lines (the name of the cell lines is indicated at the top of graphs). 4,000 cells/well were seeded in 96-well plates and 24 hours later treated or not with H-1PV (MOI: pfu/cell) and/or ABT-737 (ABT) at the indicated concentrations. 72 hours after infection, cell lysis was analyzed by LDH assay as described in the materials and methods section. Columns represent the mean values from 3 replicates with relative standard deviation bars.
Figure 2B:
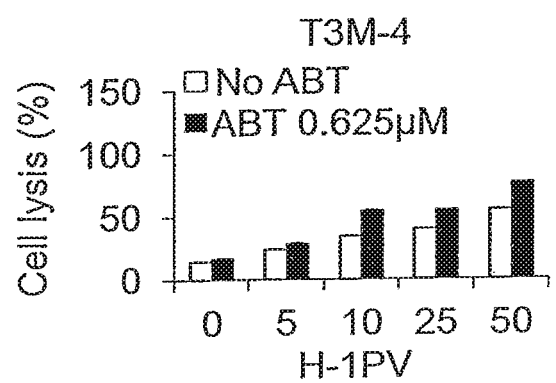
Figure 2C:
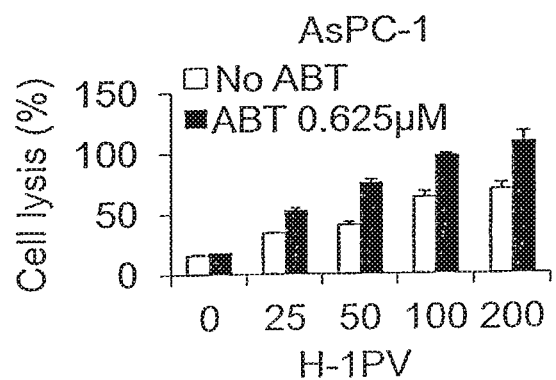
Figure 2D:
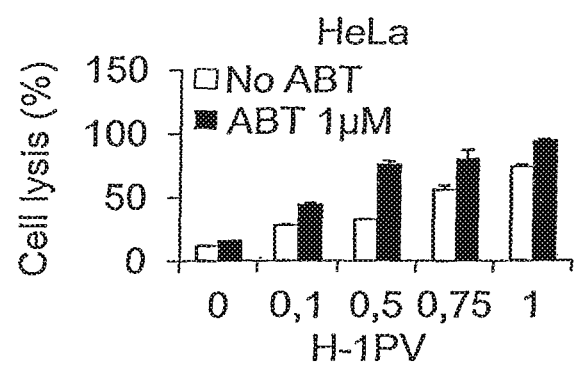
Figure 2E:
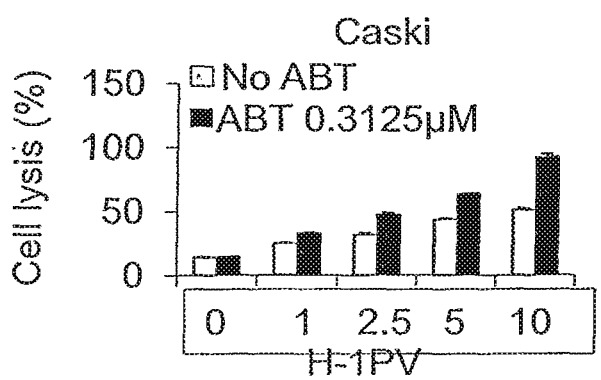
Figure 2F:
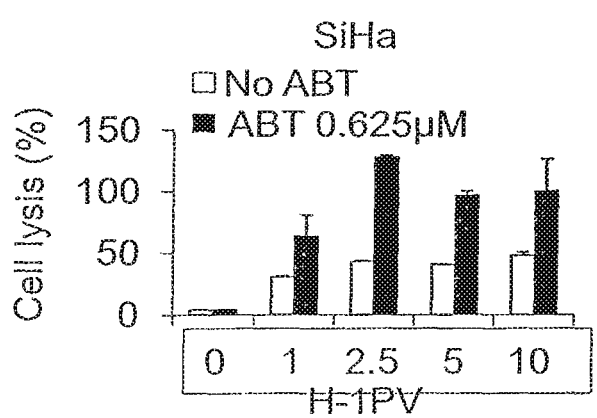
Figure 2G:
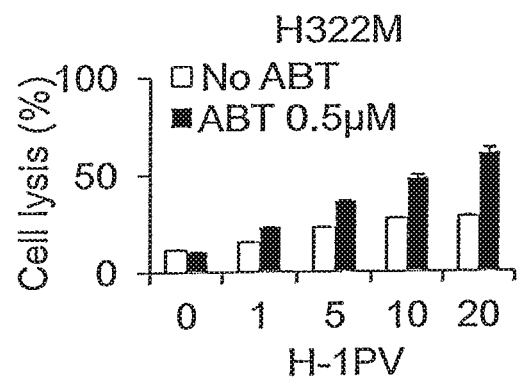
Figure 2H:
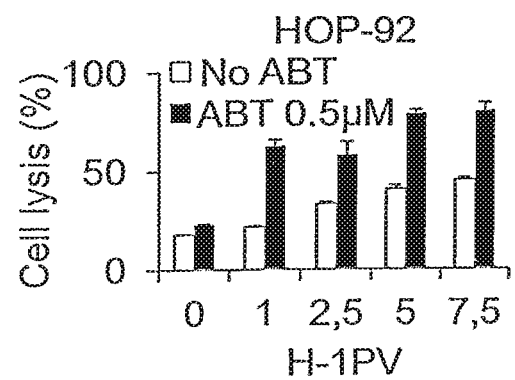
Figure 2I:
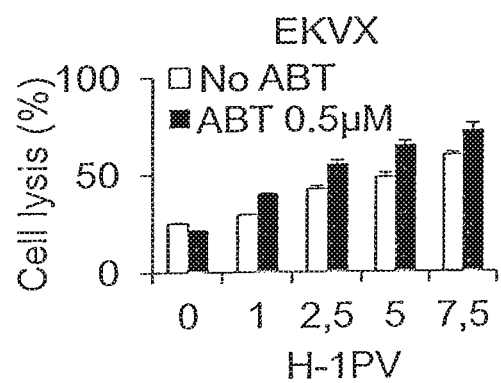
Figure 2J:
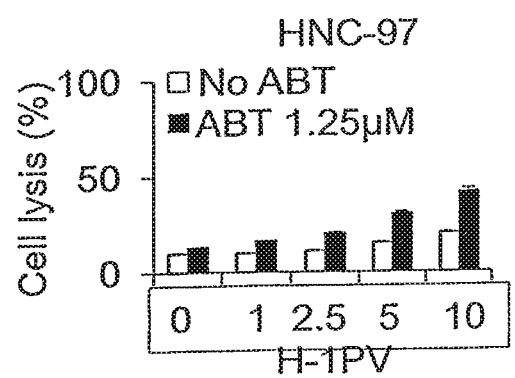
Figure 2K:
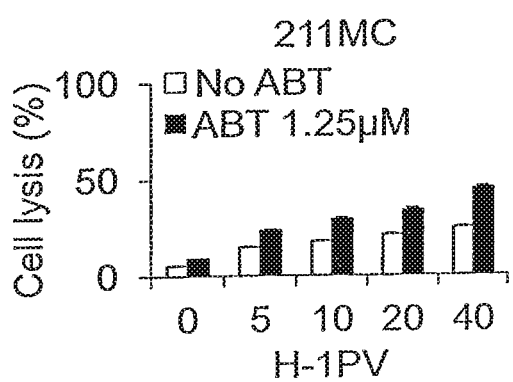
Figure 2L:
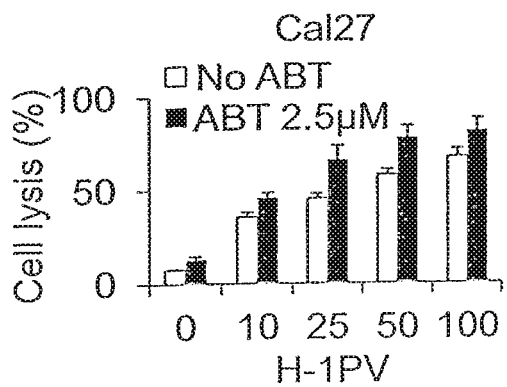
Figure 2M:
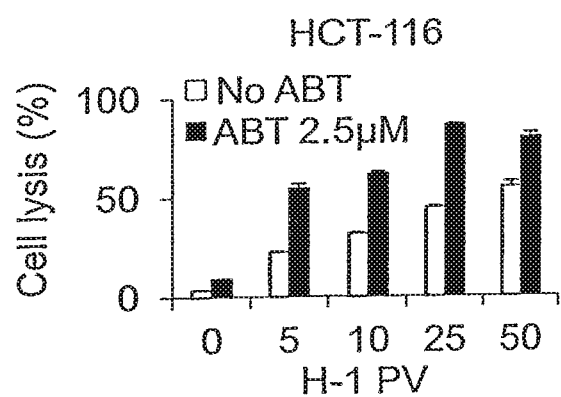
Figure 2N:
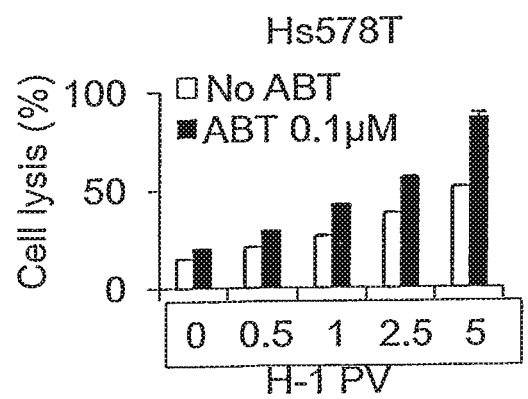
Figure 3A:
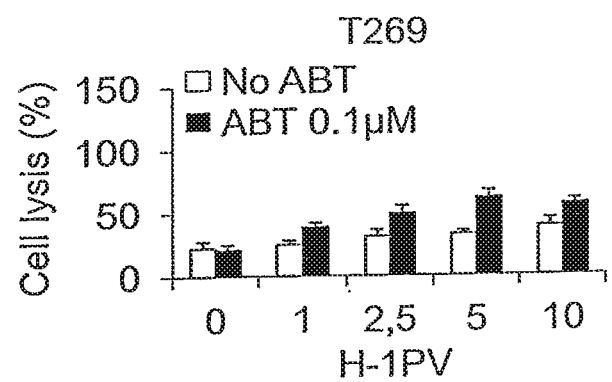
FIGS. 3A-E: ABT-737 enhances H-1PV induced cytotoxicity against cancer stem cells (CSC) in a synergistic manner LDH assays. H-1PV/ABT-737 co-treatment was tested against CSCs isolated from glioblastoma multiforme (GBM) tumours (a-c) and from cancer cell lines derived from patient with GBM (U87, d) and cervical carcinoma (HeLa, e). 10,000 cells/well were seeded in 96-well plates and after 24 hours treated or not with the indicated concentrations of H-1PV (MOI: pfu/cell) and/or ABT-737 (ABT). 72 hours after infection, cell lysis was analyzed by LDH assay as described in the materials and methods section. Columns represent the mean values from 3 replicates with relative standard deviation bars.
Figure 3B:
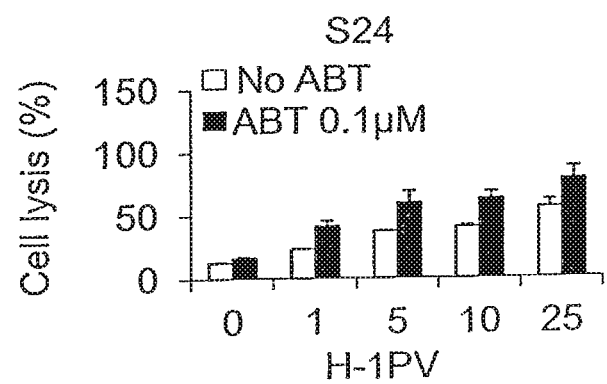
Figure 3C:
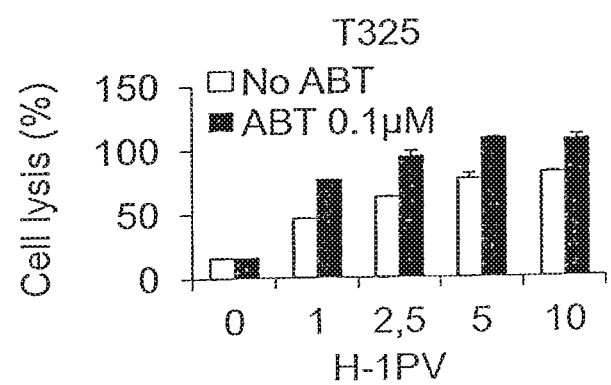
Figure 3D:
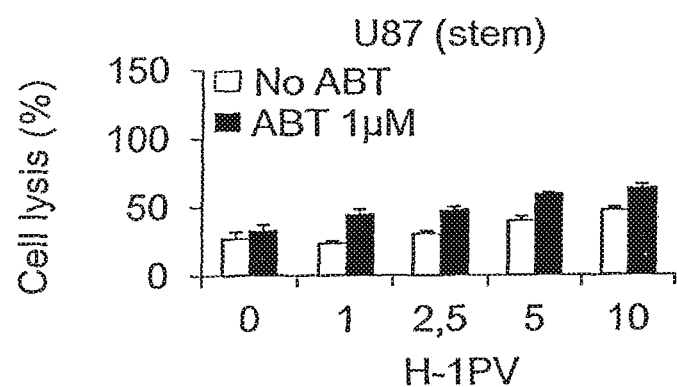
Figure 3E:
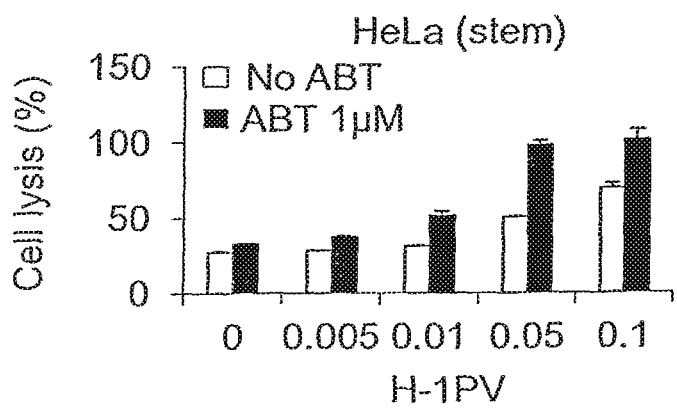
Figure 5A:
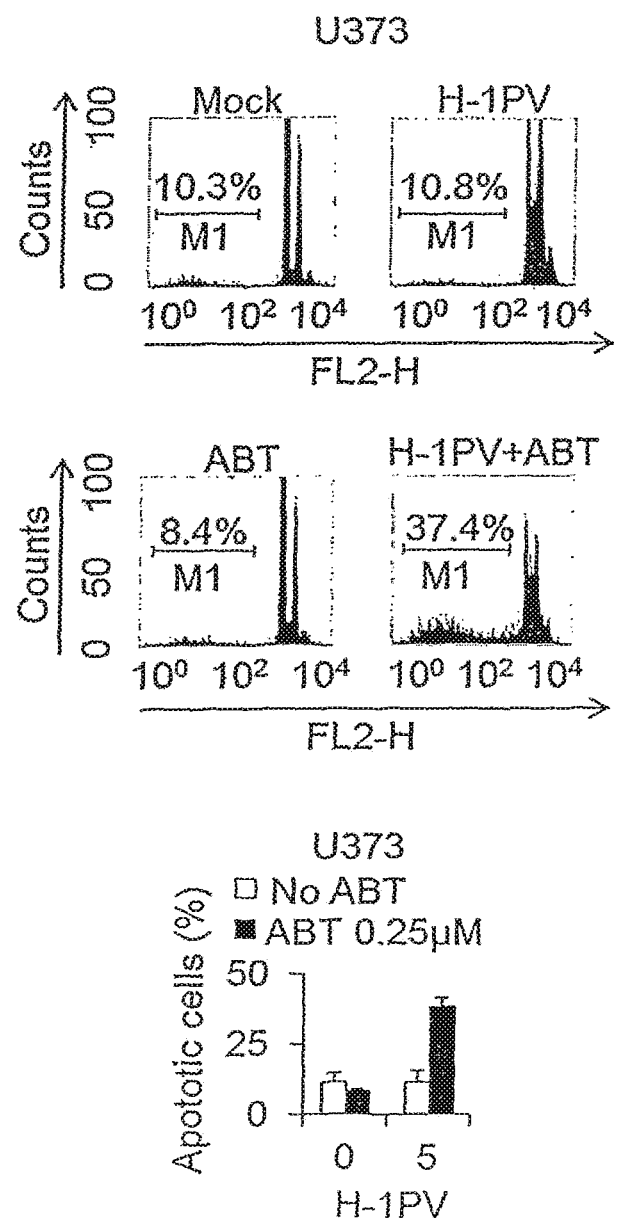
FIGS. 5A-H: ABT-737 enhances H-1PV-induced apoptosis in a synergistic manner
Figure 5B:
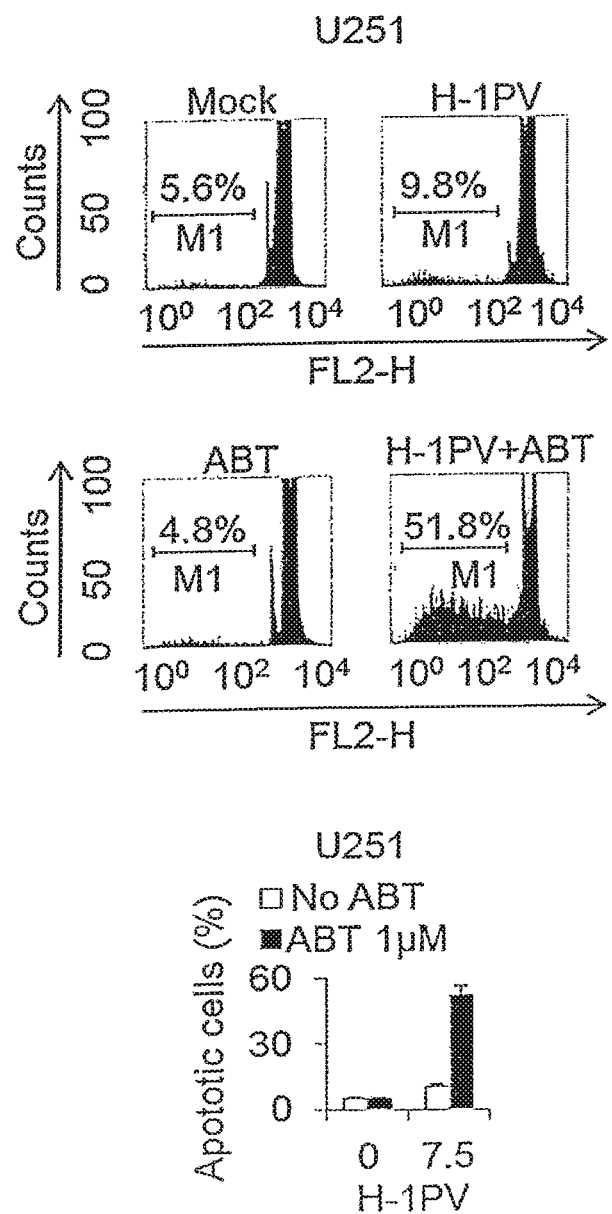
Figure 5C:
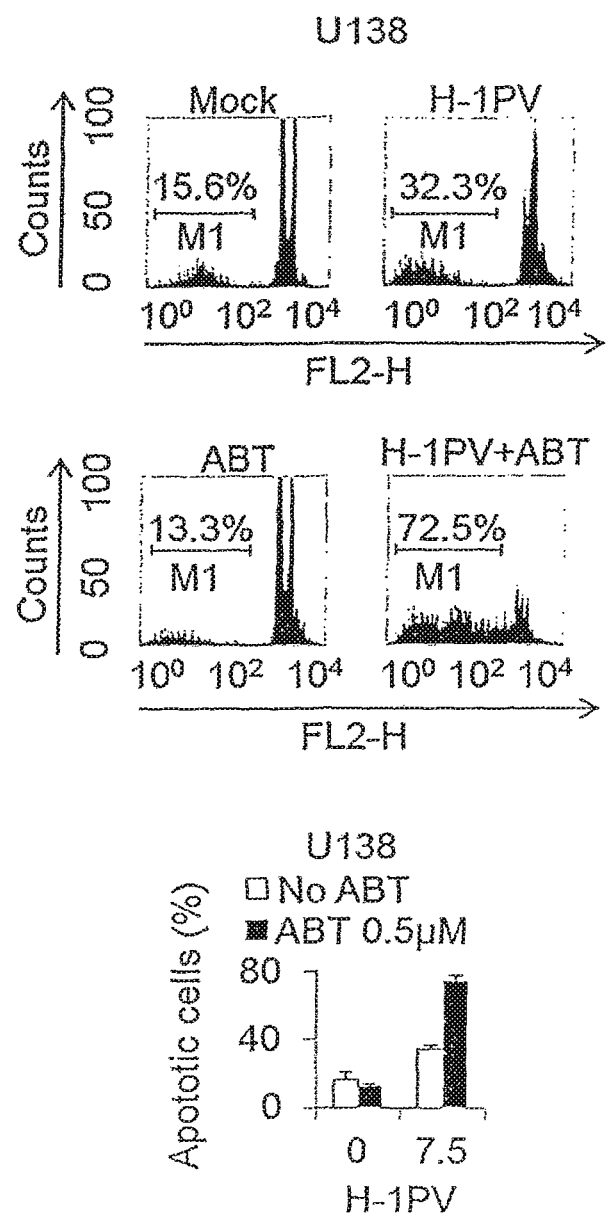
Figure 5D:
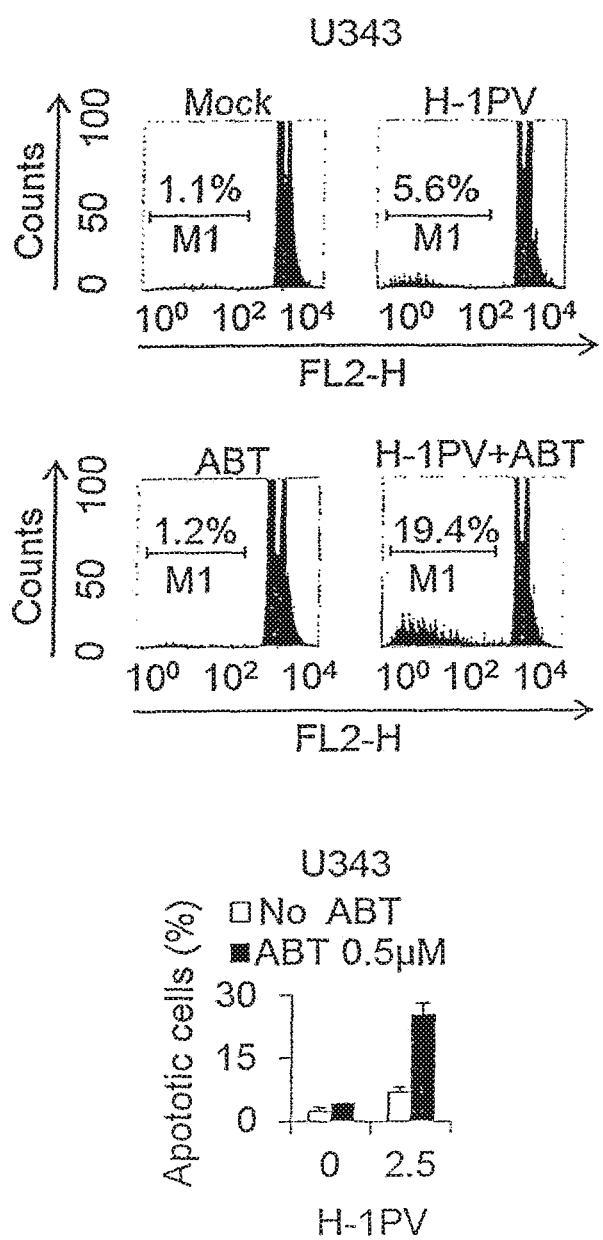
Figure 5E:
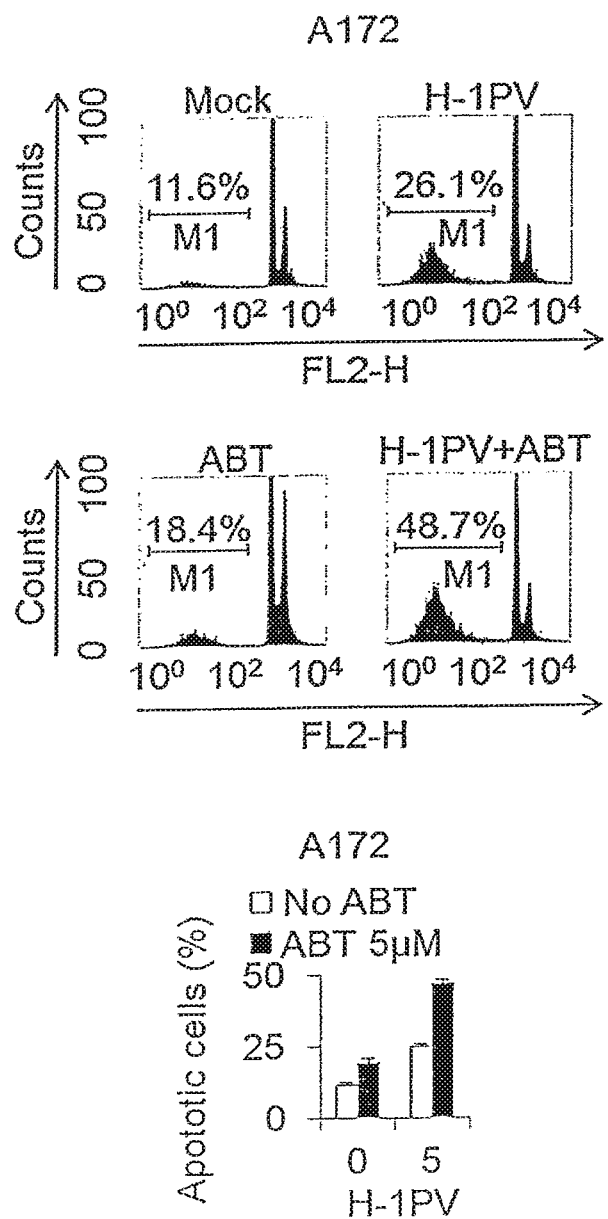
Figure 5F:
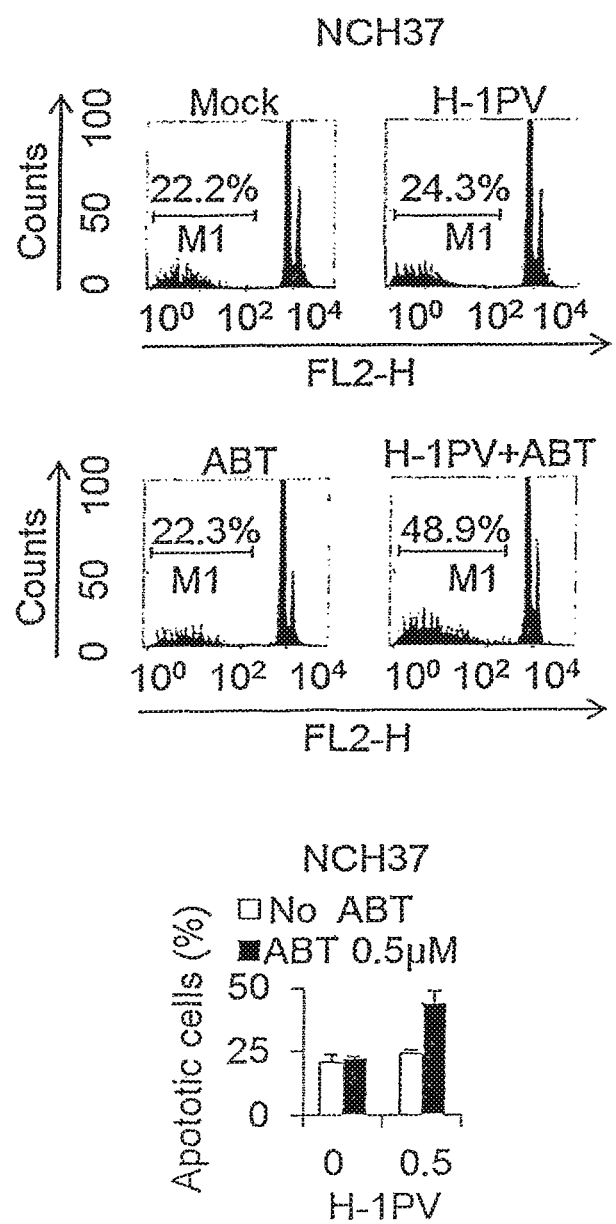
Figure 5G:
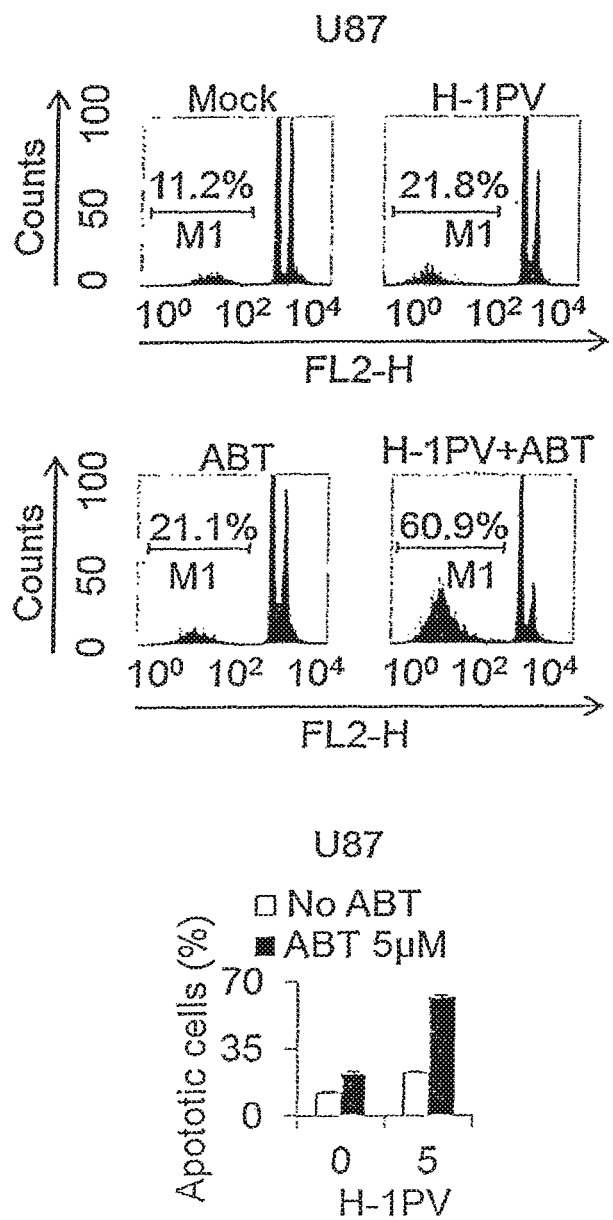
Figure 5H:
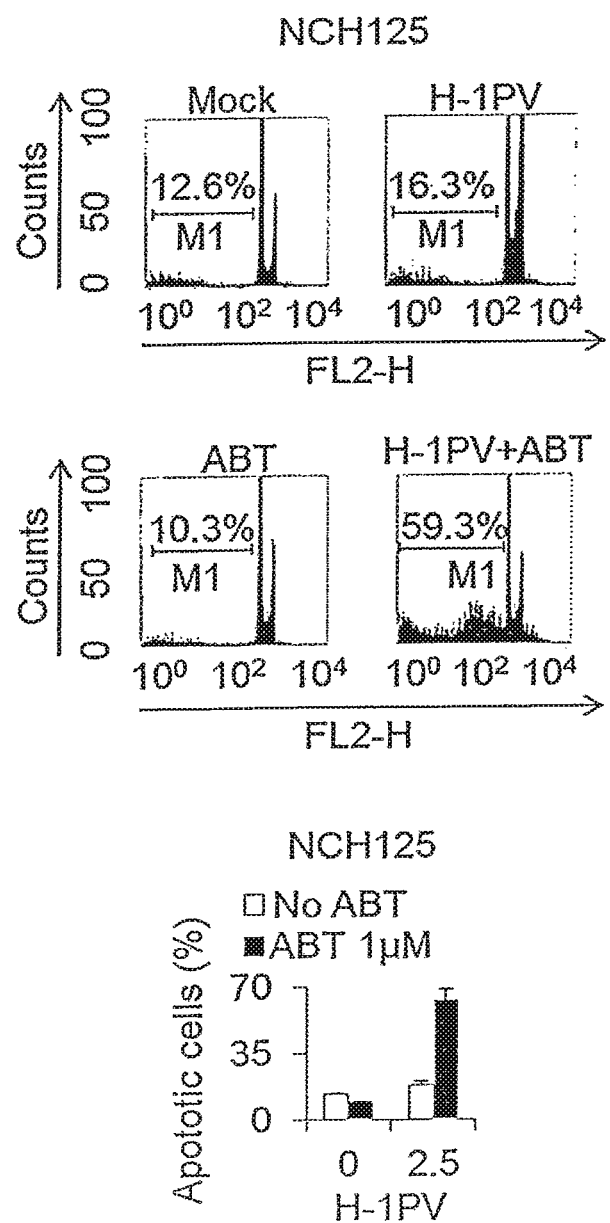
Figure 6A:
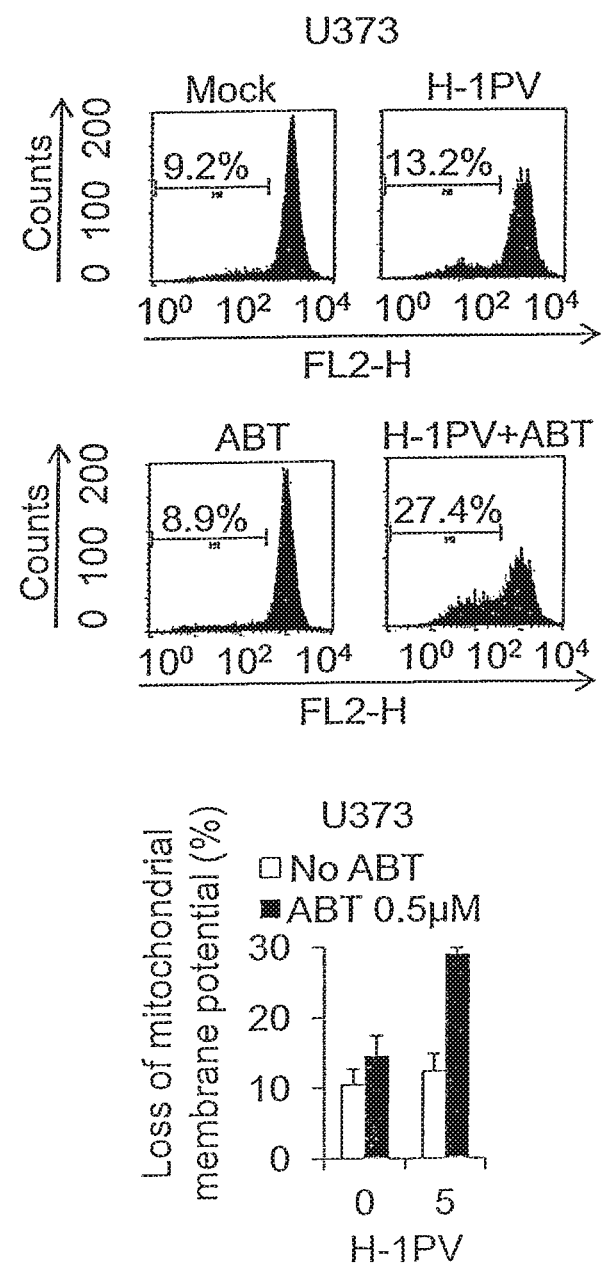
Figure 6B:
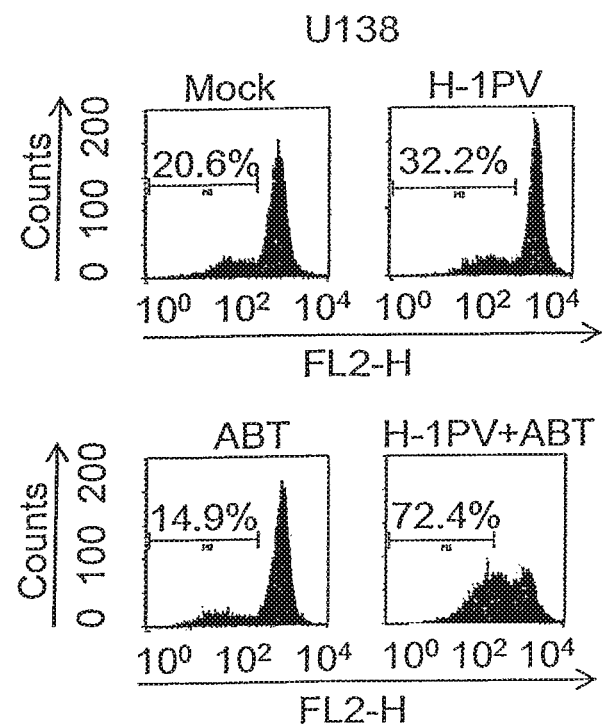
Figure 6B:
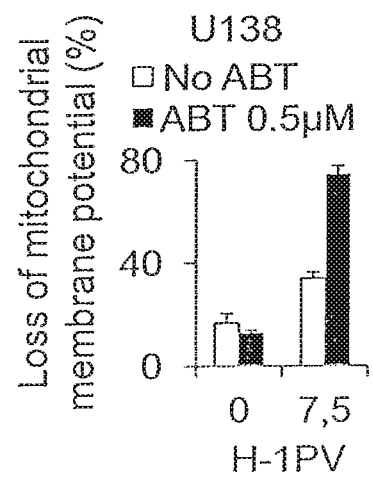
Figure 6C:
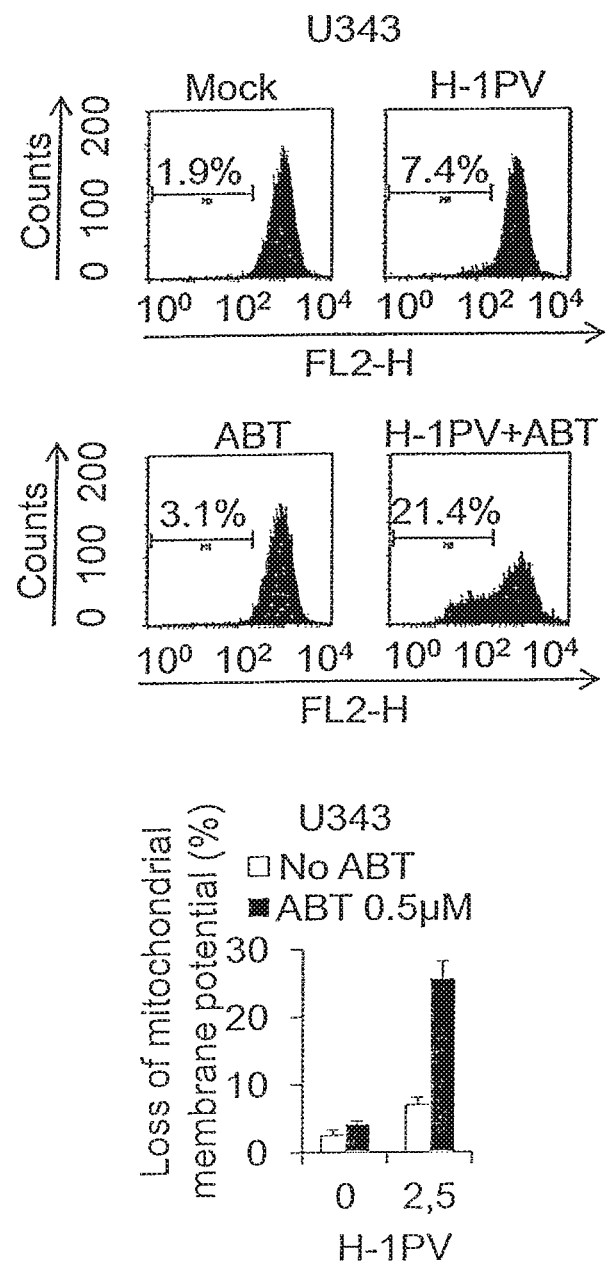
Figure 6D:
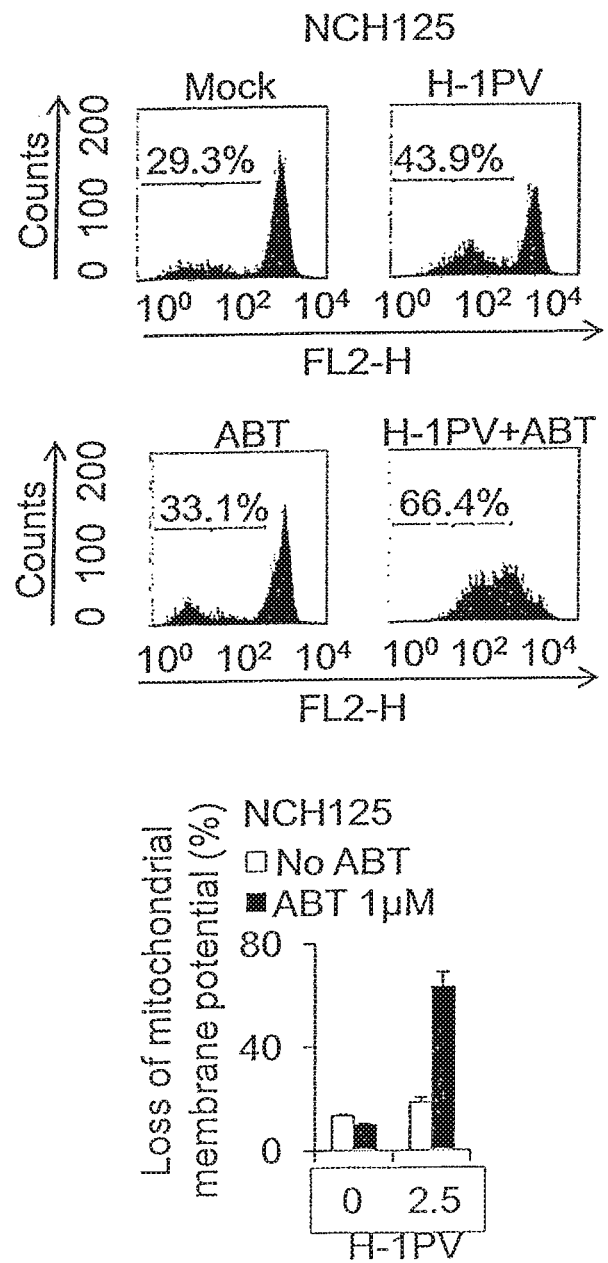
Figure 7A:
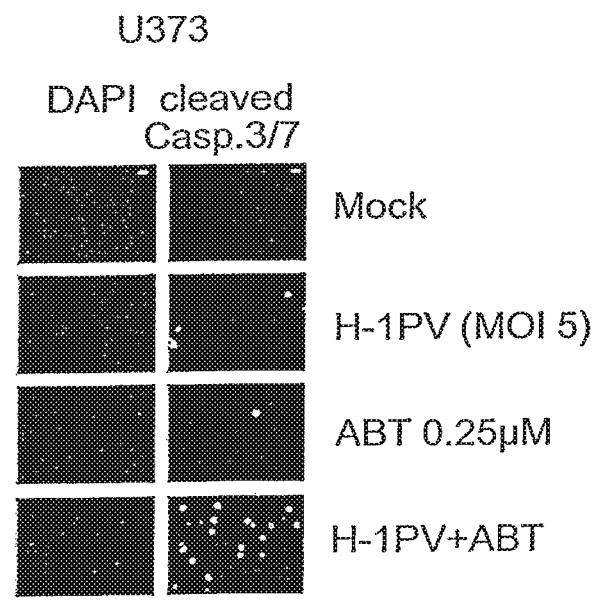
Figure 7B:
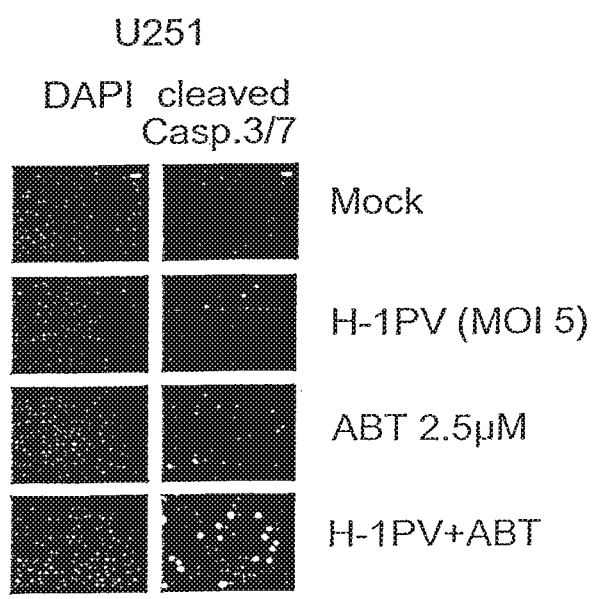
Figure 7C:
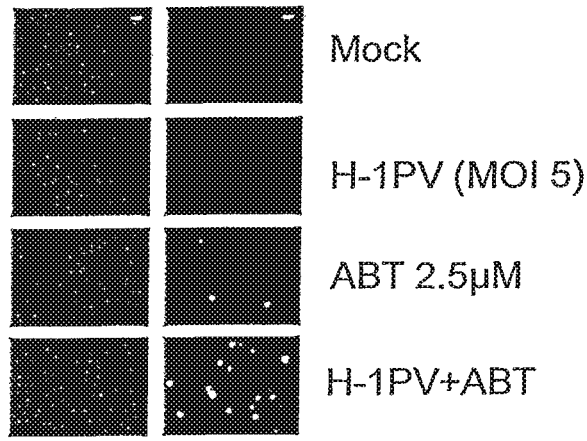
Figure 7D:
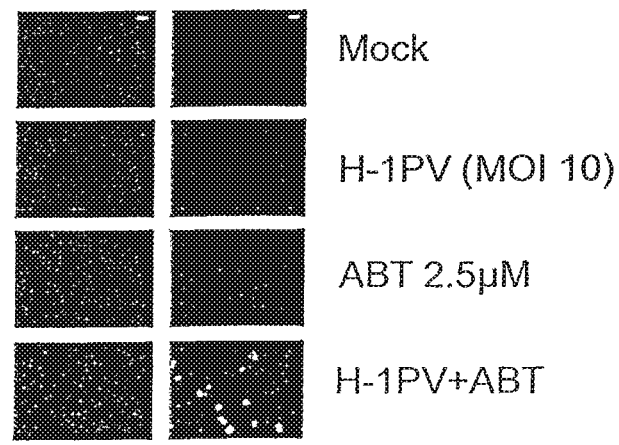
Figure 7E:
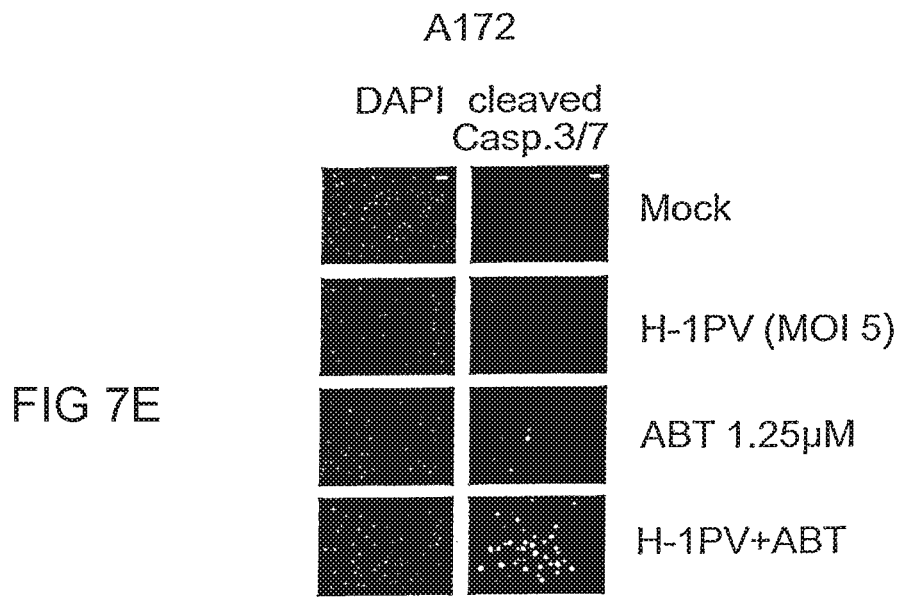
Figure 7F:
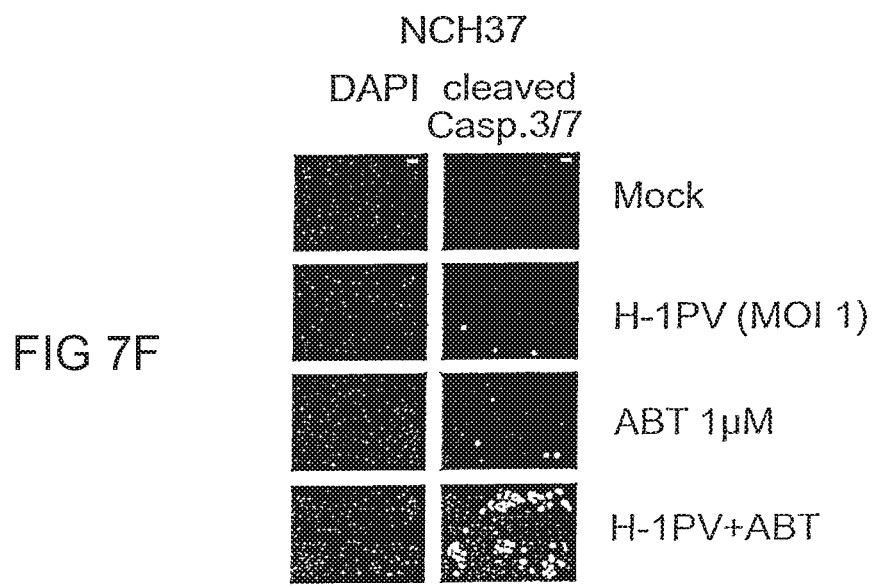
Figure 7G:
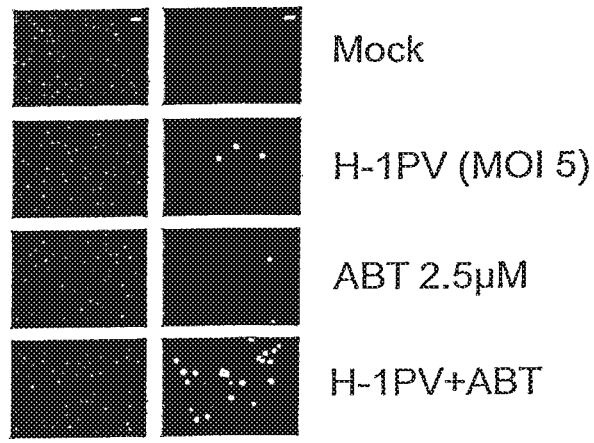
Figure 7H:
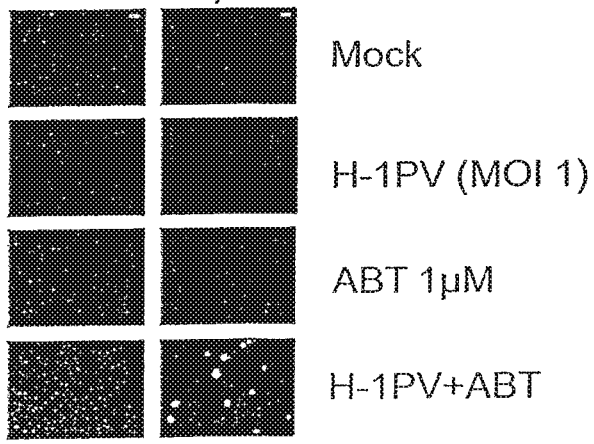

First, the H-1PV/ABT-737 co-treatment against human gliomas was evaluated. To this end a panel of eleven human cancer cell lines, ten isolated from patients with GBM (U373, LN308, U251, T98G, U138, U343, A172, LN229, U87, NCH125), and one from a patient with gliosarcoma (NCH37) was used. Cells were grown in 96-well plates and H-1PV induced cell lysis in the presence or absence of ABT-737 was analyzed by LDH assays (for experimental conditions see Table 1 and Example 1). A virus-dose dependent cell killing was observed in all cell lines tested. But cell lines varied for their susceptibility to virus infection being some cell lines like U373, LN308, U251, T98G, and U138 highly resistant to virus cytotoxicity and displaying minor cytotoxic effects even when infected with high viral multiplicity of infection (MOI, pfu/cell) (cell killing ≤25% when infected with H-1PV at MOI=10) (FIG. 1a-e), others such as U343, A172 and LN229 showing an intermediate phenotype (25-50% cell killing) (FIG. 1f-h) and others such as NCH37, U87 and NCH125 that were found sensitive to virus cytotoxicity (more than 50% cell killing) (FIG. 1i-k). ABT-737 alone at the dosages used had no apparent cytotoxicity for the cells with the only exception of glioma U87 where modestcytotoxic effects were observed (FIG. 1). Remarkably, these amounts of ABT-737 were sufficient to enhance H-1PV oncolysis in all the cell lines tested in a statistical significant synergistic manner, increasing in numerous cases viral cytotoxicity by more than 100-200%. Importantly even less sensitive cell lines such as U343 (4.7-fold increase in H-1PV induced cell killing when cells were infected with H-1PV at MOI=10 in presence of ABT-737), U138 (3.5-fold increase) and LN308 (3.2-fold increase) became susceptible to virus cytotoxic effects and efficiently killed in the presence of ABT-737 (FIG. 1).

Second, it was investigated whether the H-1PV/ABT-737 co-treatment was also efficient in killing cancer cells from other tumour entities. The following 14 human cancer cell lines were chosen for the LDH assays: pancreatic ductal adenocarcinoma (PDAC), MIA PaCa-2, T3M-4 and AsPC-1, cervical carcinoma (CC) HeLa, CaSki and SiHa, lung carcinoma (LC) H322M, HOP92 and EKVX, head and neck cutaneous squamous cell carcinoma (HNSCC), HNC97, 211MC and Ca127, colon colorectal carcinoma HCT-116 and breast cancer Hs578T cell lines. In agreement with the results obtained with the glioma cell lines, ABT-737 stimulated H-1PV induced oncolysis in a synergistic way in all cancer cell lines tested irrespective from their origin (FIG. 2).

Cancer stem cells (CSC) most likely are responsible for tumour maintenance, aggressiveness and recurrence. Therefore, in a third step the capacity of the H-1PV/ABT-737 co-treatment in lysing CSC isolated from fresh tumours (GBM T269, S24 and T325) and from cancer cell lines derived from patient with GBM (U87) and CC (HeLa) was evaluated. CSCs were propagated as tumour spheres before to be infected with H-1PV in combination or not with ABT-737. H-1PV was able to infect efficiently the different CSC cultures (data not shown). Also in this case, ABT-737 increased H-1PV cytotoxicity (FIG. 3).

Finally, it was checked whether H-1PV/ABT-737 co-treatment was safe for normal human primary cells. Normal primary fibroblasts (oral and foreskin), melanocytes and astrocytes were infected with H-1PV in combination or not with ABT-737 and then subjected to MTT (cell viability) assays (data not shown) and LDH (cell lysis) assays. Even if the virus and ABT-737 were used at high concentrations (MOI 100 and 40 respectively) and for a longer time (96 instead of the 72 hours) the massive cytotoxicity observed against cancer cells was not observed. These results provide important evidence that the two agents in combination are not harmful for normal primary cells (FIG. 4).

In conclusion, these results show for the first time that the combinatorial use of H-1PV and the Bcl-2 inhibitor ABT-737 may be a valid approach against cancer.

Example 3

H-1PV/ABT-737 Co-Treatment Induces Apoptosis Via Mitochondrial Membrane Permeabilization and Activation of Caspases ABT-737 blocks the activity of anti-apoptotic Bcl-2 molecules restoring apoptosis in cancer cells (Cragg et al, 2009).

However, to exert cytopathic effects the drug must be used at higher concentrations than those ones used in earlier experiments (Tagscherer et al, 2008). On the other hand it is known that H-1PV may induce multiple cell death programs ranging from apoptosis to necrosis to cathepsin mediated cell death (Nuesch et al, 2012). The ability of H-1PV to induce apoptosis in the presence or absence of ABT-737 was checked in a selection of eight glioma cell lines (U373, U251, U138, U343, A172, NCH37, U87, NCH125) by assessing the occurrence of DNA fragmentation by flow cytometric analysis (detection of the sub-G1 cell population). Untreated or ABT-737 treated cells infected or not with H-1PV were harvested and stained with propidium iodide. At the concentrations used in the experiments, ABT-737 and H-1PV single treatments were unable to induce apoptosis efficiently. On the contrary, when used in combination the two agents were very effective in triggering apoptosis as deduced by the strong increase of the sub-G1 population observed in all cell lines analyzed (4.7-fold increase in U251, 3.8-fold increase in U343, 3.4-fold increase in U373 and NCH125, 2.8-fold increase in U87, 2.1-fold increase in U138, 1.9-fold increase in A172 and 1.8-fold increase in NCH37 when H-1PV single treatment was compared with H-1PV/ABT-737 combination (FIG. 5).

Mitochondria play a central role in the intrinsic apoptotic pathway and mitochondrial membrane permeabilization (MMP) is a hallmark of apoptosis. MMP is mainly controlled by Bcl-2 family members. The question was addressed whether H-1PV/ABT-737-induced apoptosis involves activation of the mitochondrial apoptotic pathway. U373, U138, U343 and NCH125 glioma cell lines were infected or not with H-1PV in the presence or absence of ABT-737. After 48-96 hours, cells were stained with MitoTracker Red and analyzed by flow cytometry for MMP (FIG. 6). While ABT-737 single treatment had almost no effect on the MMP and infection with H-1PV alone was associated only with a slight MMP, H-1PV/ABT-737 co-treatment dramatically enhanced MMP (2-fold increase in U373, 2.1-fold in U138, 3.6-fold increase in U343 and 3.4-fold in NCH125 when H-1PV single treatment was compared with H-1PV/ABT-737 combination), indicating involvement of the mitochondria in the co-treatment-induced apoptosis.

Then, the role of caspases 3 and 7 in H-1PV/ABT-737-induced apoptosis was investigated. Glioma cells previously analysed by FACS analysis for the presence of apoptotic sub-G1 cell population, were stained with the CellEvent® Caspase-3/7 Green Detection Reagent which detects active forms of effector caspases 3 and 7. In agreement with previous results, a strong increase in apoptosis in all eight H-1PV/ABT-737 co-treated glioma cell lines was observed (FIG. 7).

Example 4

ABT-199 Enhances the Oncolytic Activity of H-1PV Although Less Efficiently than ABT-737

ABT-199 is a more specific, and potent inhibitor than ABT-737 against Bcl-2 but in contrast to ABT-737 is unable to target $Bcl-X_L$ and Bcl-w (Souers et al, 2013). In this experiment, it was investigated whether ABT-199 is also able to enhance the oncolytic activity of H-1PV. The LDH experiment was performed using the human glioblastoma cell line U138. Cells were infected or not with H-1PV and grown in the presence or absence of ABT-737 or ABT-199. As previously found, ABT-737 enhanced H-1PV cytotoxicity in a synergistic manner with a 3.8-fold increase in comparison to virus alone (at MOI 5) treatment. ABT-199 was also able to increase the cytotoxic activity of the virus although to a less extent than ABT-737 (1.7-fold increase) (FIG. 8). This difference in boosting H-1PV cytotoxicity may be due to the fact that U138 cells in addition to Bcl-2 also express high levels of the antiapoptotic $Bcl-X_L$ and Bcl-w which are also targets of ABT-737 but not ABT-199. Nevertheless, the use of ABT-199 in combination with the virus may be considered valuable in view of a superior safety profile, especially in cancers which express low levels of $Bcl-X_L$ and Bcl-w.

Example 5

H-1PV/ABT-737 Co-Treatment Eradicates Established Tumours

In order to validate the H-1PV/ABT-737 synergism in vivo, the inventors used the AsPC-1 xenograft nude rat model of human pancreatic carcinoma [Li et al., 2013]. H-1PV and ABT-737 alone, at the doses used, failed to have a significant therapeutic effect (rats were sacrificed when tumours reached the maximum tolerable size of 4000 mm³). In contrast, combination treatment resulted in a strong synergistic effect leading to complete and durable tumour remission in all co-treated animals (FIG. 9). No loss of weight or other adverse side effects were documented in any of the treated animals.

In conclusion, the results of the above examples show for the first time that the combinatorial use of a parvovirus (e.g. H-1PV) and a Bcl-2 inhibitor (e.g. ABT-737) may be a valid approach against cancer, in particular gliomas and pancreatic carcinomas.

The invention is further described by the following numbered paragraphs:

1. Pharmaceutical composition containing (a) a parvovirus and (b) a Bcl-2 inhibitor, wherein said parvovirus is H-1 (H-1PV) or a related rodent parvovirus selected from LuIII, Mouse minute virus (MMV), Mouse parvovirus (MPV), Rat minute virus (RMV), Rat parvovirus (RPV) or Rat virus (RV).
2. The pharmaceutical composition of paragraph 1 containing (a) the parvovirus and (b) the Bcl-2 inhibitor as separate entities.
3. The pharmaceutical composition according to paragraph 1 or 2, wherein said Bcl-2 inhibitor is ABT-737 or ABT-199.
4. Parvovirus and a Bcl-2 inhibitor as defined in any one of paragraphs 1 to 3 for use in a method of treating cancer.
5. Parvovirus and a Bcl-2 inhibitor as defined in any one of paragraphs 1 to 3 for the use according to paragraph 4 characterized in that the parvovirus and the Bcl-2 inhibitor are sequentially administered.
6. Parvovirus and a Bcl-2 inhibitor as defined in any one of paragraphs 1 to 3 for the use according to paragraph 4 or 5 characterized in that the use is for treating solid tumours and/or cancer initiating stem cells.
7. Parvovirus and a Bcl-2 inhibitor as defined in any one of paragraphs 1 to 3 for the use according to any of paragraphs 4 to 6 characterized in that the use is for treating tumours resistant to parvovirus cytotoxicity.
8. Parvovirus and a Bcl-2 inhibitor as defined in any of paragraphs 1 to 3 for use according to any of paragraphs 4 to 7, wherein the tumour is a brain tumour, pancreatic carcinoma, cervical carcinoma, lung cancer, head and neck cancer, breast cancer or colon cancer.

9. Parvovirus and a Bcl-2 inhibitor as defined in any one of paragraphs 1 to 3 for the use according to any of paragraphs 4 to 8 characterized in that the use is for treating a glioma or recurrent glioblastoma multiforme.

10. Parvovirus and a Bcl-2 inhibitor as defined in any one of paragraphs 1 to 3 for the use according to any one of paragraphs 4 to 9 characterized in that the parvovirus and/or the Bcl-2 inhibitor are administered by intratumoral administration.

LIST OF REFERENCES

Andersen M H, Svane I M, Kvistborg P, Nielsen O J, Balslev E, Reker S, Becker J C, Straten P T (2005) Immunogenicity of Bcl-2 in patients with cancer. Blood 105: 728-734

Bajwa N, Liao C, Nikolovska-Coleska Z (2012) Inhibitors of the anti-apoptotic Bcl-2 proteins: a patent review. Expert opinion on therapeutic patents 22: 37-55

Breitbach C J, Burke J, Jonker D, Stephenson J, Haas A R, Chow L Q, Nieva J, Hwang T H, Moon A, Patt R et al (2011) Intravenous delivery of a multi-mechanistic cancer-targeted oncolytic poxvirus in humans. Nature 477: 99-102

Chen C, Wei Y, Hummel M, Hoffmann T K, Gross M, Kaufmann A M, Albers A E (2011) Evidence for Epithelial-Mesenchymal Transition in Cancer Stem Cells of Head and Neck Squamous Cell Carcinoma. PLoS ONE 6: e16466

Cotmore S F, Tattersall P (2007) Parvoviral host range and cell entry mechanisms. Adv Virus Res 70: 183-232

Cragg M S, Harris C, Strasser A, Scott C L (2009) Unleashing the power of inhibitors of oncogenic kinases through BH3 mimetics. Nat Rev Cancer 9: 321-326

Daeffler L, Horlein R, Rommelaere J, Miesch J P F (2003) Modulation of Minute Virus of Mice Cytotoxic Activities through Site-Directed Mutagenesis within the NS Coding Region. Journal of Virology 77: 12466-12478

Davids M S, Letai A (2012) Targeting the B-cell lymphoma/leukemia 2 family in cancer. J Clin Oncol 30: 3127-3135

Del Gaizo Moore V, Brown J R, Certo M, Love T M, Novina C D, Letai A (2007) Chronic lymphocytic leukemia requires BCL2 to sequester prodeath BIM, explaining sensitivity to BCL2 antagonist ABT-737. The Journal of Clinical Investigation 117: 112-121

Di Piazza M, Mader C, Geletneky K, Herrero y Calle M, Weber E, Schlehofer J, Deleu L, Rommelaere J (2007) Cytosolic Activation of Cathepsins Mediates Parvovirus H-1-Induced Killing of Cisplatin and TRAIL-Resistant Glioma Cells. Journal of Virology 81: 4186-4198

El-Andaloussi N, Bonifati S, Kaufmann J K, Mailly L, Daeffler L, Deryckere F, Nettelbeck D M, Rommelaere J, Marchini A (2012) Generation of an adenovirus-parvovirus chimera with enhanced oncolytic potential. J Virol 86: 10418-10431

Geletneky K, Huesing J, Rommelaere J, Schlehofer J R, Leuchs B, Dahm M, Krebs O, von Knebel Doeberitz M, Huber B, Hajda J (2012) Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12: 99

Hanahan D, Weinberg R A (2011) Hallmarks of cancer: the next generation. Cell 144: 646-674

Hristov G, Kramer M, Li J, El-Andaloussi N, Mora R, Daeffler L, Zentgraf H, Rommelaere J, Marchini A (2010) Through Its Nonstructural Protein NS1, Parvovirus H-1 Induces Apoptosis via Accumulation of Reactive Oxygen Species. J Virol 84: 5909-5922

Li, J., Bonifatit, S., Hristov, G., Marttila, T., Valmary-Degano, S., Stanzel, S., Schnolzer, M., Mougin, C., Aprahamian, M., Grekova, S., Raykov, Z., Rommelaere, J., Marchini, A., (2013), Synergistic combination of valproic acid and oncolytic parvovirus H-1PV as a potential therapy against cervical and pancreatic carcinomas, EMBO Mol. Med. 5: 1537-1555

Morita E, Nakashima A, Asao H, Sato H, Sugamura K (2003) Human Parvovirus B19 Nonstructural Protein (NS1) Induces Cell Cycle Arrest at G1 Phase. Journal of Virology 77: 2915-2921

Nuesch J P, Lacroix J, Marchini A, Rommelaere J (2012) Molecular pathways: rodent parvoviruses—mechanisms of oncolysis and prospects for clinical cancer treatment. Clin Cancer Res 18: 3516-3523

Ohshima T, Iwama M, Ueno Y, Sugiyama F, Nakajima T, Fukamizu A, Yagami K (1998) Induction of apoptosis in vitro and in vivo by H-1 parvovirus infection. The Journal of general virology 79 (Pt 12): 3067-3071

Oltersdorf T, Elmore S W, Shoemaker A R, Armstrong R C, Augeri D J, Belli B A, Bruncko M, Deckwerth T L, Dinges J, Hajduk P J et al (2005) An inhibitor of Bcl-2 family proteins induces regression of solid tumours. Nature 435: 677-681

Ran Z, Rayet B, Rommelaere J, Faisst S (1999) Parvovirus H-1-induced cell death: influence of intracellular NAD consumption on the regulation of necrosis and apoptosis. Virus Res 65: 161-174

Rayet B, Lopez-Guerrero J A, Rommelaere J, Dinsart C (1998) Induction of programmed cell death by parvovirus H-1 in U937 cells: connection with the tumor necrosis factor alpha signalling pathway. J Virol 72: 8893-8903

Riccardi C, Nicoletti I (2006) Analysis of apoptosis by propidium iodide staining and flow cytometry. Nat Protoc 1: 1458-1461

Russell S J, Peng K W, Bell J C (2012) Oncolytic virotherapy. Nat Biotechnol 30: 658-670 Samuel S, Tumilasci V., Oliere S., Nguyen T., Shamy A., Bell J., Hiscott J. (2010), VSV Oncolysis in Combination with the BCL-2 Inhibitor Obatoclax overcomes Apoptosis Resistance in Chronic Lymphatic Leukemia, Mol. Ther. 18: 2094-2103

Samuel S, Beljanski V, Van Grevenynghe J, Richards S, Ben Yebdri F, He Z, Nichols C, Belgnaoui S M, Steel C, Goulet M L et al (2013) BCL-2 Inhibitors Sensitize Therapy-resistant Chronic Lymphocytic Leukemia Cells to VSV Oncolysis. Mol Ther 21: 1413-1423

Souers A J, Leverson J D, Boghaert E R, Ackler S L, Catron N D, Chen J, Dayton B D, Ding H, Enschede S H, Fairbrother W J et al (2013) ABT-199, a potent and selective BCL-2 inhibitor, achieves antitumor activity while sparing platelets. Nat Med 19: 202-208

Tagscherer K E, Fassl A, Campos B, Farhadi M, Kraemer A, Bock B C, Macher-Goeppinger S, Radlwimmer B, Wiestler O D, Herold-Mende C et al (2008) Apoptosis-based treatment of glioblastomas with ABT-737, a novel small molecule inhibitor of Bcl-2 family proteins. Oncogene 27: 6646-6656

Ueno Y, Harada T, Iseki H, Ohshima T, Sugiyama F, Yagami K (2001) Propagation of rat parvovirus in thymic lymphoma cell line C58(NT)d and subsequent appearance of a resistant cell clone after lytic infection. J Virol 75: 3965-3970

Vogler M, Weber K, Dinsdale D, Schmitz I, Schulze-Osthoff K, Dyer M J S, Cohen G M (2009) Different forms of cell death induced by putative BCL2 inhibitors. Cell Death Differ 16: 1030-1039

Wrzesinski C, Tesfay L, Salome N, Jauniaux J-C, Rommelaere J, Cornelis J, Dinsart C (2003) Chimeric and Pseudotyped Parvoviruses Minimize the Contamination of Recombinant Stocks with Replication-Competent Viruses and Identify a DNA Sequence That Restricts Parvovirus H-1 in Mouse Cells. Journal of Virology 77: 3851-3858

Youle R J, Strasser A (2008) The BCL-2 protein family: opposing activities that mediate cell death. Nat Rev Mol Cell Biol 9: 47-59

Yu S-c, Ping Y-f, Yi L, Zhou Z-h, Chen J-h, Yao X-h, Gao L, Wang J M, Bian X-w (2008) Isolation and characterization of cancer stem cells from a human glioblastoma cell line U87. Cancer Letters 265: 124-134

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A pharmaceutical combination comprising: (a) a parvovirus; and (b) a Bcl-2 inhibitor, wherein said parvovirus is H-1 (H-1PV) or a related rodent parvovirus selected from the group consisting of LuIII, Mouse minute virus (MMV), Mouse parvovirus (MPV), Rat minute virus (RMV), Rat parvovirus (RPV) and Rat virus (RV).

2. The pharmaceutical combination according to claim 1, wherein the parvovirus and the Bcl-2 inhibitor are separate entities.

3. The pharmaceutical combination according to claim 1, wherein said Bcl-2 inhibitor is ABT-737 or ABT-199.

\* \* \* \* \*